United States Patent
Tolleshaug et al.

(10) Patent No.: US 8,273,325 B2
(45) Date of Patent: Sep. 25, 2012

(54) CONTRAST AGENTS

(75) Inventors: Helge Tolleshaug, Olso (NO); Alan Cuthbertson, Oslo (NO); Hege Karlsen, Oslo (NO)

(73) Assignee: GE Healthcare AS, Olso (NO)

( * ) Notice: Subject to any disclaimer, the term of this patent is extended or adjusted under 35 U.S.C. 154(b) by 388 days.

(21) Appl. No.: 12/519,183

(22) PCT Filed: Dec. 19, 2007

(86) PCT No.: PCT/NO2007/000451
§ 371 (c)(1), (2), (4) Date: Jun. 15, 2009

(87) PCT Pub. No.: WO2008/075968
PCT Pub. Date: Jun. 26, 2008

(65) Prior Publication Data
US 2010/0111865 A1    May 6, 2010

(30) Foreign Application Priority Data

Dec. 20, 2006 (NO) .................................. 20065919
Oct. 4, 2007 (NO) .................................. 20075020

(51) Int. Cl.
*A61K 51/00* (2006.01)
*A61M 36/14* (2006.01)

(52) U.S. Cl. ..................... 424/1.69; 424/1.11; 424/1.65; 424/9.1; 424/9.6

(58) Field of Classification Search ................. 424/1.11, 424/1.65, 1.69, 1.81, 1.85, 1.89, 9.1, 9.2, 424/9.3, 9.4, 9.5, 9.6, 9.7, 9.8; 534/7, 10–16; 514/1, 1.11; 530/300, 324–338
See application file for complete search history.

(56) References Cited

U.S. PATENT DOCUMENTS 6,592,847 B1 * 7/2003 Weissleder et al. ............ 424/9.6

OTHER PUBLICATIONS

PCT/NO2007/000451 ISRWO dated May 2008.

* cited by examiner

*Primary Examiner* — D L Jones

(57) ABSTRACT

The present invention provides novel compounds and pharmaceutical compositions containing such compounds, wherein the compounds have affinity for proteoglycans. The compounds comprise an amino acid based core unit linked to positively charged moieties. The compounds further comprise at least one imaging moiety detectable in in vivo imaging making the compounds useful as diagnostic contrast agents for imaging of proteoglycans, such as heparan sulphate proteoglycans.

14 Claims, No Drawings

CONTRAST AGENTS

This application is a filing under 35 U.S.C. §371 of International Application Number PCT/NO2007/000451, filed Dec. 19, 2007, which claims priority to Norwegian application numbers 20065919 filed Dec. 20, 2006 and 20075020 filed Oct. 4, 2007, each of which is hereby incorporated by reference in its entirety.

TECHNICAL FIELD OF THE INVENTION

The present invention relates to a class of compounds and pharmaceutical compositions containing such compounds having affinity for proteoglycans. More specifically the compounds may be used as contrast agents targeting to such proteoglycans.

The invention further relates to the use of the pharmaceutical compositions as mentioned above as contrast agents in diagnostic imaging.

BACKGROUND OF THE INVENTION

Proteoglycans are macromolecules distributed in the body. Proteoglycans can be found intracellular, on the surface of the cells and in the extracellular matrix. Proteoglycans represent a special class of glycoproteins that are heavily glycosylated. They consist of a core protein with one or more covalently attached glycosaminoglycan chain(s). These glycosaminoglycan (GAG) chains are long, linear carbohydrate polymers that are negatively charged under physiological conditions, due to the occurrence of sulphate and uronic acid groups.

Heparan sulphate proteoglycans (HSPG) is one group of proteoglycans. These comprise repeating disaccharides (GAGs) of D-glucuronic acid (GlcUA) and N-acetylglucosamine (GlcNAc) linked to a core protein. The size of an individual GAG can reach 100 kDa. The GAGs are highly negatively charged due to the presence of sulphate or carboxyl groups or both on many of the sugar residues, resulting in that the HSPGs are overall negatively charged.

Glycosaminoglycans (GAGs) or mucopolysaccharides are long unbranched polysaccharides consisting of a repeating disaccharide unit. This unit consists of an N-acetyl-hexosamine and a hexose or hexuronic acid, either or both of which may be sulfated. Members of the glycosaminoglycan family vary in the type of hexosamine, hexose or hexuronic acid unit they contain (e.g. glucuronic acid, iduronic acid, galactose, galactosamine, glucosamine). They also vary in the geometry of the glycosidic linkage. This family of carbohydrates is essential or important for the life of vertebrates and of various lower animals.

GAGs form an important component of connective tissues.

An upregulation of proteoglycans is associated with various diseases and conditions such as Alzheimer's disease, aneurismal aortas, atherosclerosis, hepatic fibrosis, microvascular endothelia and cancers such as breast cancer, cervical cancer, colon carcinoma, colorectal cancer, pancreatic cancer, prostate cancer and Wilm's tumour.

A number of research groups have been active in finding product and procedures for the identification of proteoglycans in vivo as illustrated by the following publications:

WO 00/23109 (The Regents of the University of California) proposes diagnostic agents for human cancers comprising a binding molecule, in particular an antibody, which is attached to a reporting molecule, and that binds to one of glypican-1 and to syndecan-1.

US 2002/0122806 (Chinnaiyan et al.) proposes a chimeric molecule, e.g. a recombinant polypeptide and a pharmaceutical composition comprising a fluorescent or chemiluminescent polypeptide and a chondroitin sulphate proteoglycan binding polypeptide and its use in diagnostic imaging.

WO 88/03413 (New England Deaconess Hospital) reads on a target seeking, biologically active molecule associated with an abnormality in the vascular system labelled with a radionuclide or a magnetic resonance imaging entity. The biologically active antibody has affinity e.g. for chondroitin sulphate proteoglycan and the antibody is preferably a monoclonal antibody.

WO 91/13919 (New England Deaconess Hospital) relates to peptides derived from vascular-associated protein having affinity for a vascular wall component which can be a proteoglycan and which can be labelled with a detectable label.

U.S. Pat. No. 6,991,778 (Nitrosci) proposes a MR imaging method for enhancing the imaging of joints using a water-soluble positive charged nitroxyl-functionalized dendrimer for visualisation of proteoglycans of the cartilage present in the joints.

Proteoglycans, and particularly HSPGs are attractive markers for diagnosis of various diseases as noted above. The efficient targeting and imaging of HSPGs demands a vector with high affinity for the target structure that is chemically robust and stable. These conditions are met by the compounds of the invention.

SUMMARY OF THE PRESENT INVENTION

The present invention provides novel compounds and pharmaceutical compositions containing such compounds, which compounds have affinity for proteoglycans. The compounds comprise a core unit linking positively charged moieties. The compounds further comprise at least one imaging moiety detectable in in vivo imaging making the compounds useful as diagnostic contrast agents for imaging of proteoglycans and thereby useful in the diagnoses of medical conditions such as degenerative diseases, cardiovascular diseases and cancers.

Pharmaceutical compositions comprising the compounds of the present invention, use thereof and a method of imaging are also part of the invention.

DETAILED DESCRIPTION OF THE INVENTION

In a first embodiment, the present invention provides compounds having affinity for proteoglycans defined by formula I, and pharmaceutically acceptable salts thereof, $$R-S_p-C-(L-P)_n \qquad (I)$$

wherein

C represents a core unit linked to the L unit and to the S unit when S is present or to the R moiety when S is not present, and which comprises amino acid residues;

L is the same or different and represents a bifunctional linker unit;

P is the same or different and represents a positively charged peptide unit;

S represents a spacer unit;

R represents an imaging moiety;

p represents an integer of 0 or 1;

n represents an integer from 1 to 16;

The various aspects of the invention are further specified in the attached claims.

C represents a core unit which is linked to the L unit and to the S unit when S is present or to the R moiety when S is not present, and which comprises amino acid residues of natural and non-natural amino acids and optionally amines. The amino acids are D or L amino acids and preferably D amino acids. The amino acids lysine, ornithine, diaminopropionic acid and also amines such as those of the formulas:

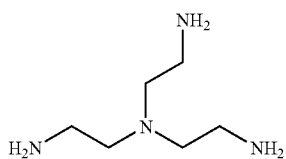

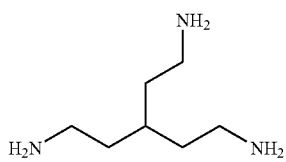

are preferred. The amine groups are preferably grafted on to the amino acid chains. Preferably C contains 2 to 16 amino acid residues, and most preferred 2 to 8.

Even more preferred the unit C comprises lysine residues, and optionally also further units, such as other amino acids containing functional groups facilitating site specific conjugation to the unit L and to unit S or moiety R. Examples of such functional groups are $NH_2$, OH, SH, $ONH_2$, $NHNH_2$.

In a particularly preferred embodiment the unit C contains 2 to 4 amino acid residues. The amino acid residues are most preferably lysine residues where any free C terminal carboxyl residue may be functionalised by the formation of an amide residue.

Examples of the preferred C unit includes lys-lys-$NH_2$ lys-lys(lys)-lys-$NH_2$ The core unit C can also include units that modify the biodistribution of the compound of formula (I). Such units are denoted biomodifier units. Thus, the introduction of e.g. an ether will help to minimise plasma protein binding. Biomodifier units may also comprise a polyethyleneglycol (PEG) building block or a peptide chain of 1 to 10 amino acid residues or a combination thereof, and function to modify the pharmacokinetics and blood clearance rates of the compound of formula (I) in vivo. The presence of such biomodifier units accelerates or reduces the clearance of the imaging agent from background tissue, such as muscle or liver, and/or from the blood, thus giving a better diagnostic image due to less background interference. When used to increase blood residence time, this is beneficial for maximising the probability of the compound interacting with the targeting entity at the site of pathology. A biomodifier unit may also be used to favour a particular route of excretion, e.g. via the kidneys as opposed to via the liver.

As noted above, L is the same or different and represents a bifunctional linker unit which links the P unit to the C unit, preferably L is neutral or negatively charged. PEG linker units are to preferred. The PEG linkers may be functionalised at the end groups to facilitate binding to the C and P units. Examples of such functionalisation comprise carboxylation and amidation.

When L comprises a PEG unit, it preferably comprises units derived from oligomerisation of the monodisperse PEG-like structure 17-amino-5-oxo-6-aza-3,9,12,15-tetraoxaheptadecanoic acid of formula (II)

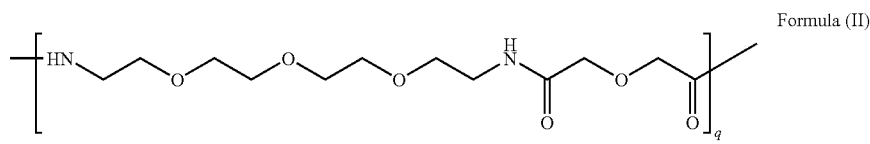

Formula (II)

wherein q equals an integer from 1 to 10 and which binds to the carboxy and the amino entities of amino acids.

The unit L of the formula

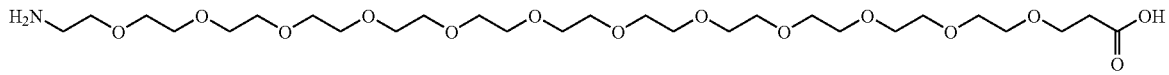

denoted "PEG 12" is also preferred.

Each of the units P are the same or different as noted above and contain up to 20 amino acids, preferably from 2 to 16 amino acids. The amino acids are D or L amino acids.

Each of the P units is overall positively charged. Hence, P comprises at least one amino acid and preferably at least two amino acids, either a usual or unusual amino acid, which are positively charged at physiological pH. P may contain amino acids that are neutral at physiological pH and optionally one or two negatively charged amino acids, as long as the P unit maintain an overall positive charge at physiological pH. Particularly preferred amino acids also encompass amino acid mimetics. In a preferred embodiment, P includes at least one amino acid selected from the group of arginine, arginine mimetics, lysine, glycine, proline, ornithine and histidine, but it will be evident to the skilled artisan that various other amino acids can be used and that the amino acid sequences can be varied depending on the to affinity of the receptor site and the pH at the binding site in vivo.

In another preferred embodiment, each unit P has at least 2 positive charges, more preferably at least 3 positive charges, and most preferably at least 4 positive charges. Overall, the compound of formula (I) should have at least 8 positive charges, and preferably from 8 to 32 positive charges.

Most preferably, P includes at least one amino acid comprising a guanidine group or a guanidine derived group. Guanidine has the formula $(H_2N)_2C\!=\!NH$ and is positively charged at neutral pH, in the form of the guanidinium ion.

Examples of amino acids comprising such guanidine group, or a guanidine derived group, are arginine, and arginine mimetics such as norArg, Phe(4-guanidine), homoarginine and transPro(4-guanidine). Other positively charged unusual amino acids may also be used. The N-terminals of the peptidic unit P may be optionally capped.

The unit S is a spacer that distances the unit C from the imaging moiety R. This is particularly important when the imaging moiety is relatively bulky, e.g. when it contains a metal complex or a radioiodine atom, so that binding of the compound of formula (I) is not impaired by the imaging moiety. This can be achieved by a combination of flexibility, e.g. by including an alkyl chain, so that the imaging moiety has the freedom to position itself away from the binding site. Units S may be the same or similar to units L, i.e. it may be a PEG unit.

The imaging moiety R comprises an "imaging entity" which is detectable either external to the mammalian body or via use of detectors designed for use in vivo, such as intravascular radiation or optical detectors such as endoscopes, or radiation detectors designed for intra-operative use.

Preferred imaging entities are those which can be detected externally in a non-invasive manner following administration in vivo of a compound of formula (I). Preferably R comprises an imaging entity imageable in the MR, SPECT, PET, optical or X-ray imaging modalities. Most preferred are radioactive imaging entities and especially radioactive metal ions, gamma-emitting radioactive halogens and positron-emitting radioactive non-metals, particularly those suitable for imaging using SPECT or PET. Imaging entities comprising dyes for optical imaging are also particularly preferred.

The imaging moiety may consist of the imaging entity itself bound directly to the S or C unit of formula (I), e.g. a non-metallic chemical entity such as a halogen atom or a dye. When the imaging entity is a metallic compound, e.g. a metal ion, the imaging entity is part of the imaging moiety that is bound to S or C, e.g. a complexing agent. In this situation, the imaging moiety R comprises the imaging entity.

The imaging entity is preferably chosen from:
(i) a radioactive metal ion;
(ii) a paramagnetic metal ion;
(iii) a gamma-emitting radioactive halogen;
(iv) a positron-emitting radioactive non-metal;
(v) a hyperpolarised NMR-active nucleus;
(vi) a reporter suitable for in vivo optical imaging;
(vii) a β-emitter suitable for intravascular detection.

When the imaging entity is a radioactive metal ion, ie. a radiometal, the term radiometal includes radioactive transition elements and lanthanides and actinides, and metallic main group elements. The semi-metals arsenic, selenium and tellurium are excluded. Suitable radio metals can be either positron emitters such as $^{64}Cu$, $^{48}V$, $^{52}Fe$, $^{55}Co$, $^{94m}Tc$ or $^{68}Ga$; gamma-emitters such as $^{99m}Tc$, $^{111}In$, $^{113}In$, or $^{67}Ga$. Preferred radio metals are $^{99m}Tc$, $^{64}Cu$, $^{68}Ga$ and $^{111}In$. Most preferred radio metals are gamma-emitters, especially $^{99m}Tc$.

When the imaging entity is a paramagnetic metal ion, suitable such metal ions include: Gd(III), Mn(II), Cu(II), Cr(III), Fe(III), Co(II), Er(II), Ni(II), Eu(III) or Dy(III). Preferred paramagnetic metal ions are Gd(III), Mn(II) and Fe(III), with Gd(III) being especially preferred.

When the imaging entity is a gamma-emitting radioactive halogen, the radiohalogen is suitably chosen from $^{123}I$, or $^{77}Br$. A preferred gamma-emitting radioactive halogen is $^{123}I$.

When the imaging entity is a positron-emitting radioactive non-metal, suitable such positron emitters include: $^{11}C$, $^{13}N$, $^{15}O$ $^{17}F$ $^{18}F$ $^{75}Br$ $^{76}Br$ or $^{124}I$. Preferred emitting radioactive non-metals are $^{11}C$, $^{13}N$, $^{18}F$ and $^{124}I$, especially $^{11}C$ and $^{18}F$, most especially $^{18}F$.

When the imaging entity is a hyperpolarised NMR-active nucleus, such NMR-active nuclei have a non-zero nuclear spin, and include $^{13}C$, $^{15}N$, $^{19}F$, $^{29}Si$ and $^{31}P$. Of these, $^{13}C$ is preferred. By the term "hyperpolarised" is meant enhancement of the degree of polarisation of the NMR-active nucleus over its equilibrium polarisation. The natural abundance of $^{13}C$ (relative to $^{12}C$) is about 1%, and suitable $^{13}C$-labelled compounds are suitably enriched to an abundance of at least 5%, preferably at least 50%, most preferably at least 90% before being hyperpolarised.

When the imaging entity is a reporter suitable for in vivo optical imaging, the reporter is any entity capable of detection either directly or indirectly in an optical imaging procedure. The reporter might be a light scatterer (e.g. coloured or uncoloured particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most preferably the reporter has fluorescent properties.

Preferred organic chromophoric and fluorophoric reporters include groups having an extensive delocalized electron system, eg. cyanines, merocyanines, indocyanines, phthalocyanines, naphthalocyanines, triphenylmethines, porphyrins, pyrilium dyes, thiapyriliup dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo, dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful. Complexes of certain rare earth metals (e.g. europium, samarium, terbium or dysprosium) are used in certain contexts, as are fluorescent nanocrystals (quantum dots).

Particular examples of chromophores which may be used include:
fluorescein, sulforhodamine 101 (Texas Red), rhodamine B, rhodamine 6G, rhodamine 19, indocyanine green, Cy2, Cy3, Cy3.5, Cy5, Cy5.5, Cy5**, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750, and derivatives thereof.

Particularly preferred are dyes which have absorption maxima in the visible or near infrared region, between 400 nm and 3 μm, particularly between 600 and 1300 nm. Optical imaging modalities and measurement techniques include, but are not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferomeky; coherence interferometry; diffuse optical tomography and fluorescence mediated diffuse optical tomography (continuous wave, time domain and frequency domain systems), and measurement of light scattering, absorption, polarization, luminescence, fluorescence lifetime, quantum yield, and quenching.

When the imaging entity is a β-emitter e.g. suitable for intravascular detection, such β-emitters include the radiometals $^{67}$Cu, $^{89}$Sr, $^{90}$Y, $^{183}$Sm, $^{186}$Re, $^{188}$Re or $^{192}$Ir, and the non-metals $^{32}$P, $^{33}$P, $^{38}$S, $^{38}$Cl, $^{39}$Cl, $^{82}$Br and $^{83}$B.

When the imaging moiety comprises a metal ion, the metal ion is present as a metal complex. By the term "metal complex" is meant a coordination complex of the metal ion with one or more ligands. It is strongly preferred that the metal complex is kinetically stable and hence resistant to transchelation, i.e. does not readily undergo ligand exchange with other potentially competing ligands for the metal coordination sites.

Suitable ligands for use in the present invention which form metal complexes resistant to transchelation include: chelating agents, where 2-6, preferably 2-4, metal donor atoms are arranged such that 5- or 6-membered chelate rings result (by having a non coordinating backbone of either carbon atoms or non-coordinating heteroatoms linking the metal donor atoms); or monodentate ligands which comprise donor atoms which bind strongly to the metal ion, such as isonitriles, phosphines or diazenides. Examples of donor atom types which bind well to metals as part of chelating agents are: amines, thiols, amides, oximes and phosphines. Phosphines form such strong metal complexes that even monodentate or bidentate phosphines form suitable metal complexes. The linear geometry of isonitriles and diazenides is such that they do not lend themselves readily to incorporation into chelating agents, and are hence typically used as monodentate ligands. Examples of suitable isonitriles include simple alkyl isonitriles such as tert-butylisonitrile, and ether-substituted isonitriles such as mibi (i.e. 1-isocyano-2-methoxy-2-methylpropane). Examples of suitable phosphines include Tetrofosmin, and monodentate phosphines such as tris(3-methoxypropyl)phosphine. Examples of suitable diazenides include the HYNIC series of ligands i.e. hydrazine-substituted pyridines or nicotinamides.

Preferred ligands are chelating agents, and monodentate ligands which form kinetically stable metal complexes such as phosphines, isonitriles and diazenides. Most preferred ligands are chelating agents, as defined above.

Examples of suitable chelating agents for technetium which form metal complexes resistant to transchelation include, but are not limited to:

(i) diaminedioximes of formula (III):

Formula (III)

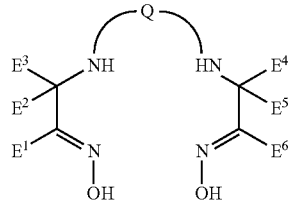

where $E^1$-$E^6$ are each independently an R' group; each R' is H or $C_{1-10}$ alkyl, $C_{3-10}$ alkylaryl, $C_{2-10}$ alkoxyalkyl, hydroxyalkyl, $C_{1-10}$ fluoroalkyl, $C_{2-10}$ carboxyalkyl or $C_{1-10}$ aminoalkyl, or two or more R' groups that together with the atoms to which they are attached form a carbocyclic, heterocyclic, saturated or unsaturated ring, and wherein one or more of the R' groups is conjugated to the branching unit, and Q is a bridging group of formula -(J)$_f$- where f is 3, 4 or 5 and each J is independently —O—, —NR'— or —C(R)$_2$— provided that -(J)$_f$-contains a maximum of one J group which is —O— or —NR'—.

Preferred Q groups are as follows:
Q=—(CH$_2$)(CHR')(CH$_2$)— ie. propyleneamine oxime or PnAO derivatives;
Q=—(CH$_2$)$_2$(CHR')(CH$_2$)$_2$— ie. pentyleneamine oxime or PentAO derivatives;
Q=—CH$_2$)$_2$NR(CH$_2$)$_2$—.

$E^1$ to $E^6$ are preferably chosen from: $C_{1-3}$ alkyl, alkylaryl, alkoxyalkyl, hydroxyalkyl, fluoroalkyl, carboxyalkyl or aminoalkyl. Most preferably, each $E^1$ to $E^6$ group is $CH_3$.

The branching unit is preferably conjugated at either the $E^1$ or $E^6$ R' group, or an R' group of the Q group. Most preferably, the branching unit is conjugated to an R' group of the Q group. When the branching unit is conjugated to an R' group of the Q group, the R' group is preferably at the bridgehead position. In that case, Q is preferably —(CH$_2$)(CHR)(CH$_2$)—, —(CH$_2$)$_2$(CHR')(CH$_2$)$_2$— or —(CH$_2$)$_2$NR'(CH$_2$)$_2$—, most preferably —(CH$_2$)$_2$(CHR)(CH$_2$)$_2$—.

An especially preferred bifunctional diaminedioxime chelator is of the formula:
(i)

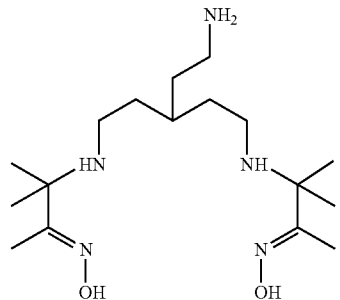

wherein one of the units C or S are conjugated via the bridgehead —CH$_2$CH$_2$NH$_2$ group.

Further preferred chelators are:
(ii) N$_3$S ligands having a thioltriamide donor set such as MAG$_3$ (mercaptoacetyltriglycine) and related ligands; or having a diamidepyridinethiol donor set such as Pica;
(iii) N$_2$S$_2$ ligands having a diaminedithiol donor set such as BAT or ECD (i.e. ethylcysteinate dimer), or an amideaminedithiol donor set such as MAMA;
(iv) N$_4$ ligands which are open chain or macrocyclic ligands having a tetramine, amidetriamine or diamidediamine donor set, such as cyclam, monoxocyclam or dioxocyclam.
(v) N$_2$O$_2$ ligands having a diaminediphenol donor set.

The above described ligands are particularly suitable for complexing technetium e.g. $^{94m}$Tc or $^{99m}$Tc, and are described more fully by Jurisson et al [Chem. Rev., 99, 2205 2218 (1999)]. The ligands are also useful for other metals, such as copper ($^{64}$Cu or $^{67}$Cu), vanadium leg. $^{48}$V), iron (e.g. $^{52}$Fe), or cobalt (e.g. $^{55}$Co). Other suitable ligands are described in Sandoz WO 91/01144, which includes ligands which are particularly suitable for indium, yttrium and gadolinium, especially macrocyclic aminocarboxylate and aminophosphonic acid ligands. Ligands which form non-ionic (i.e. neutral) metal complexes of gadolinium are known and are described in U.S. Pat. No. 4,885,363. When the radiometal ion is technetium, the ligand is preferably a chelating agent which is tetradentate. Preferred chelating agents for technetium are the diaminedioximes, or those having an N$_2$S$_2$ or N$_3$S donor set as described above.

It is preferred that the unit P is bound to the metal complex in such a way that the linkage does not undergo facile metabolism in blood, since this would result in the metal complex being cleaved off before the labelled compound has reached the desired in vivo target site. The unit P may therefore be covalently bound to the metal complexes via linkages S which are not readily metabolised.

When the imaging entity is a radioactive halogen, such as iodine, the branching unit is suitably chosen to include: a non-radioactive halogen atom such as an aryl iodide or bromide (to permit radioiodine exchange); an activated aryl ring (e.g. a phenol group); an organometallic precursor compound (ea. trialkyltin or trialkylsilyl); an organic precursor such as triazenes or a good leaving group for nucleophilic substitution such as an iodonium salt. Methods of introducing radioactive halogens (including HI and OFF) are described by Bolton [J. Lab. Comp. Radiopharm., 45, 485-528 (2002)]. Examples of suitable aryl groups to which radioactive halogens, especially iodine, can be attached are:

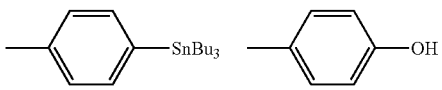

Both these entities contain substituents which permit facile radioiodine substitution onto the aromatic ring. Alternative substituents containing radioactive iodine can be synthesised by direct iodination via radiohalogen exchange. When the imaging entity is a radioactive isotope of iodine the radioiodine atom is preferably attached via a direct covalent bond to an aromatic ring such as a benzene ring or to a vinyl group, since it is known that iodine atoms bound to saturated aliphatic systems are prone to in vivo metabolism and hence loss of the radioiodine.

When the imaging moiety comprises a radioactive isotope of fluorine (e.g. $^{18}F$), the radiohalogenation may be carried out via direct labelling using the reaction of $^{18}F$-fluoride with a suitable precursor having a good leaving group, such as an alkyl bromide, alkyl mesylate or alkyl tosylate. $^{18}F$ can also be introduced by N-alkylation of amine precursors with alkylating agents such as $^{18}F(CH_2)_3OMs$ (where Ms is mesylate) to give $N-(CH_2)_3^{18}F$, or O-alkylation of hydroxyl groups with $F(CH_2)_3OMs$ or $^{18}F(CH_2)_3Br$. $^{18}F$ can also be introduced by alkylation of N-haloacetyl groups with a $^{18}F(CH_2)_3OH$ reactant, to give $-NH(CO)CH_2O(CH_2)_3^{18}F$ derivatives. For aryl systems, $^{18}F$-fluoride nucleophilic displacement from an aryl diazonium salt, an aryl nitro compound or an aryl quaternary ammonium salt are suitable routes to aryl-$^{18}F$ derivatives.

In a preferred embodiment of the invention, compounds of formula (I) as well as pharmaceutically acceptable salts are provided wherein:
the core unit C comprises amino acids lysine, ornithine, diaminopropionic acid and amines;
the linkers L are the same and comprise PEG linking units;
the units P are the same and contain 2 to 8 positive charges and up to 20 amino acids;
S is present or absent and when present comprises an alkyl chain or a PEG unit;
R comprises one of the imaging entities (i) to (vii):
(i) a radioactive metal ion;
(ii) a paramagnetic metal ion;
(iii) a gamma-emitting radioactive halogen;
(iv) a positron-emitting radioactive non-metal;
(v) a hyperpolarised NMR-active nucleus;
(vi) a reporter suitable for in vivo optical imaging;
(vii) a β-emitter suitable for intravascular detection;
p represents an integer of 0 or 1;
and
n represents an integer from 1 to 4.

The compounds of the general formula (I) can be synthesized by several synthetic pathways known to the skilled artisan and from commercially available starting materials. The units C and P can be synthesized using known methods of chemical synthesis. The solid-phase methodology of Merrifield employing an automated peptide synthesizer (J. Am. Chem. Soc., 85: 2149 (1964)) is particularly useful. Standard procedures for the synthesis strategy are described in E. Atherton & R. C. Sheppard "Solid phase peptide synthesis: a practical approach, 1989, IRL press, Oxford.

Synthesis of peptides by solid phase techniques is based upon the sequential addition of protected amino acids linked, optionally through a linker unit, to a solid phase support. In one commonly employed method, the α-amino group is suitably protected with acid labile or base labile protecting groups. Following addition and coupling of the first amino acid residue, the α-amino protecting group is removed. The chain is extended by the sequential addition of further protected amino acid derivatives or peptide fragments.

The compounds of formula (Ia)

$$S_p-C-(L-P)_n \qquad \text{Formula (Ia)}$$

wherein S, p, C, L, P and n has the meanings above and including non-peptidic linker units, S when present and P can be assembled using a fully automated synthesis procedure. In a further step, the imaging moiety R is coupled to the S or C unit by ordinary synthetic methods. As noted above, the non-metallic imaging entities can be coupled directly to the C unit, or it can be bound to a carrier, e.g. to an aryl entity for an iodine element. When the imaging entity is a metal ion, a suitable complexant is coupled to the S or C unit and the metal ion in the form of its salt or oxide is added to the compound carrying the complexant following procedures known from the state of art, e.g. in WO 03/006070.

The preparation of the compounds according to the present invention can be based on building blocks and stepwise synthesis. The core C is used as a first building block wherein said core is substituted with reactive groups which allow for the attachment of L and either $S_p$ or R, L or a precursor thereof is reacted with the substituted first building block to form a second building block consisting of the core C and L. For this reaction, L comprises a reactive group which is able to react with the reactive group of the first building block to result in the attachment of L to said first building block. In a subsequent step, P or a precursor thereof is attached to the second building block forming a third building block consisting of the core C, L and P. When present, $S_p$ or a precursor thereof is attached to the third building block forming a fourth building block consisting of the core $S_p$, C, L and P. Dependent on whether $S_p$ is present or not, R or a precursor thereof is attached to the third or fourth building block.

Thus, a method for the preparation of compounds according to the present invention comprises
a) using as a first building block a core unit C that is substituted with reactive groups which allow for the attachment of L and either $S_p$ or R;
b) reacting L or a precursor thereof with said first building block to form a second building block consisting of the core C and L;
c) reacting P or a precursor thereof with said second building block to form a third building block consisting of the core C, L and P;
d) optionally reacting $S_p$ or a precursor thereof with said third building block to form a fourth building block consisting of the core $S_p$, C, L and P;
e) reacting R or a precursor thereof with said third or fourth building block.

The compounds of formula (I) of the invention have affinity for proteoglycans. Examples of groups of proteoglycans are: Syndecan-1 and GPC1 (upregulated in pancreatic cancer), Syndecan-2 (upregulated in colon carcinoma) and Syndecan-4 (upregulated in hepatocellular carcinoma). Preferred compounds of the invention have affinity for HSPGs and target the glucosaminoglycan (GAGs) of the HSPGs by interacting with the negative charges of these. The structured peptide sequence P of the compounds of formula (I) matches the repeating stick-like structure of the GAGs forming a cross-binding targeting effect. The peptide structure P can bind several regions of one GAG chain or cross-bind to several GAG chains. This may provide a higher binding affinity than those compounds having one single positively charged peptide chain.

The imaging moiety can be detected following administration of the compound to a mammalian body in vivo. For administration the compounds of formula (I) are formulated as sterile compositions suitable for in vivo injection or as compositions suitable for oral administration or for administration into body ducts such as the rectum and the uterus.

In a second aspect, the present invention provides a pharmaceutical composition comprising the compound as described above, together with a biocompatible carrier, in a form suitable for mammalian administration. The "biocompatible carrier" is a fluid, especially a liquid, in which the compound can be suspended or dissolved, providing the composition in a physiologically tolerable form that can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is either isotonic or not hypotonic); an aqueous solution of one or more toxicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials to (e.g. polyethyleneglycols, propylene glycols and the like).

The invention further provides the use of the pharmaceutical composition in a method of diagnostic imaging. The method includes administration of the pharmaceutical composition to a human or non-human body. The body is examined with a diagnostic device and data are compiled from the examination. The data can be further processed if needed to facilitate that the data can be used to create an image and also to reach to a diagnosis. The data can be used for the visualisation and identification of diseases and conditions associated with an upregulation of proteoglycans as noted above. The compounds can be administered by injection or infusion of sterile compositions or as compositions suitable for oral administration or for administration into body ducts such as the rectum and the uterus.

In a further aspect, the present invention also provides a method of diagnostic imaging of a human or non-human body which comprises imaging of a human or non-human body which has previously been administered with the pharmaceutical composition described above. In this embodiment the pharmaceutical composition is used in a method of imaging, or imaging processing wherein the term "previously been administered" means that any step requiring a medically-qualified person to administer the composition to the patient has already been carried out.

In yet a further aspect, the present invention provides a method of generating images of a human or animal body, wherein a compound as disclosed, or a pharmaceutical composition comprising such compound, is administered to a human or non-human body, and wherein an image of at least a part of said body is generated to which said compound has been distributed.

EXAMPLES

The following abbreviations are used:
Ac: Acetyl
Arg: Arginine
Boc: tert-Butoxycarbonyl
Dde: 1-(4,4-Dimethyl-2,6-dioxocyclo hex-1-ylidene)ethyl
DMF: Dimethylformamide
Fmoc: 9-Fluorenylmethoxycarbonyl
Glu: Glutamic acid
Gly: Glycine
HATU: N-[(Dimethylamino)-1H-1,2,3-triazolo-[4,5-b]pyridine-1-ylmethylene]-N-methylmethanaminium hexafluorophosohate N-oxide
HBTU: 2-(1H-Benzotriazole-1-yl)-1,1,3,3-tetramethyluronium hexafluorophosphate
HOAt: 1-Hydroxy-7-azabenzotriazole
HPLC: High performance liquid chromatography
Lys: Lysine
NMM: 4-Methylmorpholine
Ot-Bu: Tert butoxide
Pbf: 2,2,4,6,7-Pentamethyldihydrobenzofuran-5-sulfonyl
PEG: Polyethylene glycol
PEG4: 17-amino-5-oxo-6-aza-3,9,12,15-tetraoxaheptadecanoic acid
PEG12: 39-amino-4,7,10,13,16,19,22,25,28,31,34,37-dodecaoxapropionic acid
PyAOP: [7-Azabenzotriazol-1-yloxytris(pyrrolidino)phosphonium-hexafluorophosphate
Pro: Proline
TFA: Trifluoroacetic acid
TIS: Triisopropylsilane
Rink amide (TM) a polystyrene based resin Examples 1 to 8 illustrate preparations of intermediates of formula C-(L-P)$_n$ which correspond to the compound of formula (Ia) above when p equals zero. Examples 9 to 13 illustrate compounds of formula (I).

Example 1

Synthesis of Ac-D-Arg-D-Arg-D-Arg-Gly-Gly-Gly-D-Arg-PEG12-D-Lys(PEG12-D-Arg-Gly-Gly-Gly-D-Arg-D-Arg-D-Ara-Ac)-D-Lys-NH$_2$

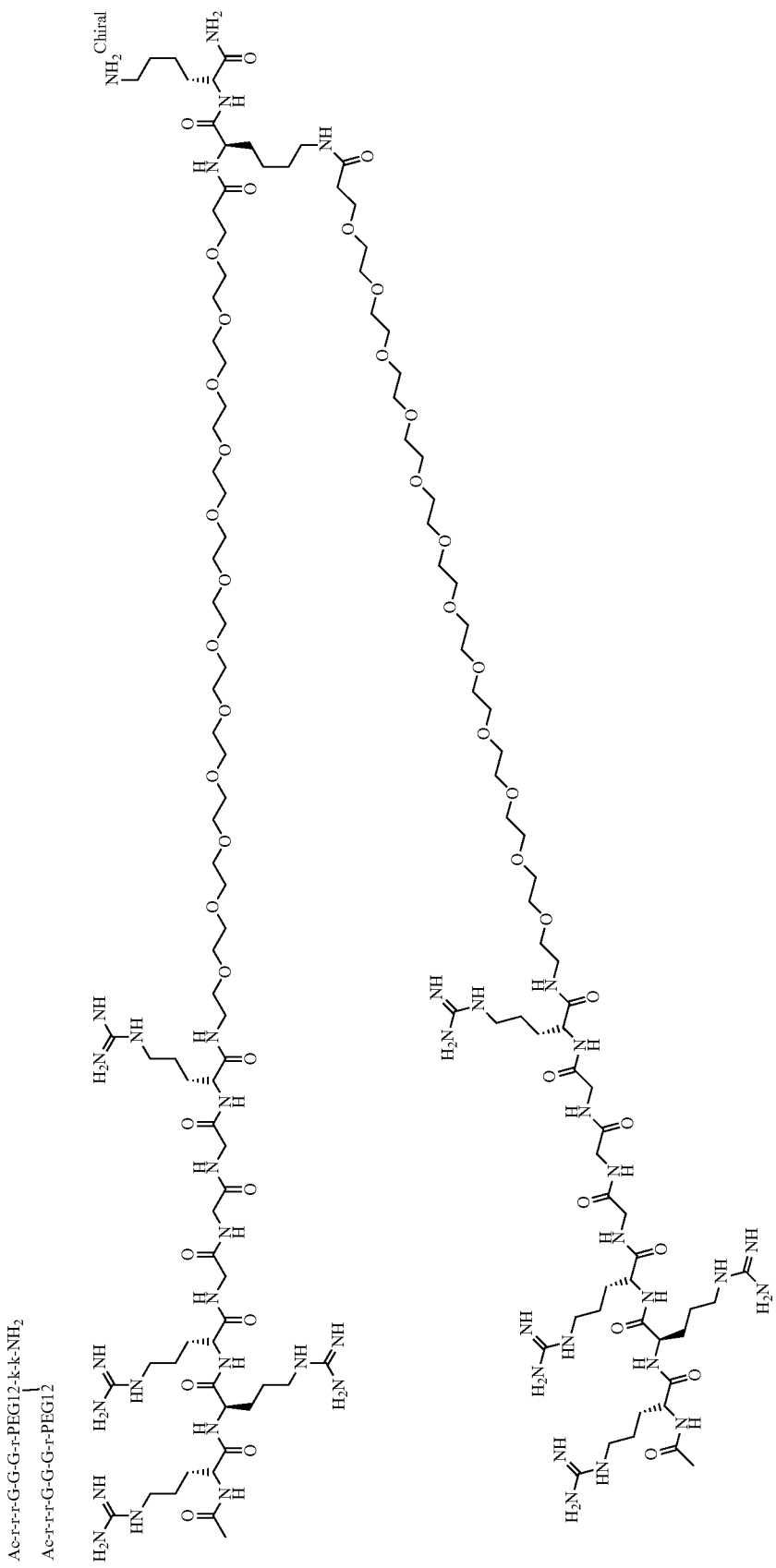

Assembly of Fmoc-D-Lys(Boc)-OH, Fmoc-D-Lys(Dde)-OH and Fmoc PEG12 was done manually starting with Rink amide MBHA resin (Novabiochem, 0.58 mmole/g; scale=0.10 mmole)=0.172 g. Removal of Fmoc groups during synthesis of the peptide was done using 20% piperidine (Fluka) in dimethylformamide (Rathburn) and the Dde protecting groups were removed using 2% Hydrazine (Aldrich) in DMF. Fmoc-D-Lys(Boc)-OH (Novabiochem, 141 mg, 0.3 mmole) was pre-activated with HATU (Applied biosystems, 114 mg, 0.3 mmole) and 4-methylmorpholine (Fluka, 66 μL, 0.6 mmole) in DMF; before it was coupled to the resin. Coupling of the next amino acids was performed the same way using Fmoc-D-Lys(Dde)-OH (Nova biochem, 266.3 mg, 0.5 mmole), HATU (Applied biosystems, 190 mg, 0.5 mmole) and 4-methylmorpholine (Fluka, 110 μL, 1.0 mmole) in DMF and 39-(Fmoc-amino)-4,7,10,13,16,19,22,25,28,31,34,37-dodecaoxapropionic acid (Polypure, 336 mg, 0.4 mmole), HATU (Applied biosystems, 152 mg, 0.4 mmole) and 4-methylmorpholine (Fluka, 88 μL, 0.8 mmole) in DMF.

Assembly of the rest of the amino acid sequence (D-Arg (Pbf)-D-Arg(Pbf)-D-Arg(Pbf)-Gly-Gly-D-Arg(Pbf)) was done using fully automated synthesis (ABI 433A) using 1 mmole amino acid cartridges from Applied biosystems. The amino acids were pre-activated using HBTU (Applied biosystems) before coupling. The resin was acetylated using acetic anhydride (Merck, 10 eq.) and 4-methylmorpholine (Fluka, 20 eq.) in DMF. The simultaneous removal of side-chain protecting groups and peptide from the resin was carried out in trifluoroacetic acid (Fluka) containing 2.5% water and 2.5% triisopropylsilane (Aldrich) for 6 hours. The resin was removed by filtration and the filtrate evaporated in vacuo. Diethyl ether (Eternell) was added to the residue. The resulting precipitate was washed with ether and air-dried. The crude product was purified using reverse phase preparative chromatography (Phenomenex Luna C18 column, 00G-4252-P0; solvents A=water/0.1% TFA and B=CH$_3$CN/0.1% TFA; gradient 10-25% B over 60 min; flow 10 ml/minute; detection at 214 and 254 nm), Characterisation was done using analytical HPLC: Phenomenex Luna C18 column, 00G-4252-E0; solvents: A=water+0.1% TFA/B=CH$_3$CN+0.1% TFA, gradient: 10-25% B over 20 min; flow 1.0 ml/minute; retention time 11.8 minutes, detected at 214 and 254 nm). Further characterisation was carried out using mass spectrometry, giving m/z value 1050.7 [M-3H+].

Example 2

Synthesis of Ac-D-Arg-D-Arg-D-Arg-Gly-Gly-Gly-D-Arg-Gly-D-Glu-PEG12-D-Lys(PEG12-D-Glu-Gly-D-Arg-Gly-Gly-Gly-D-Arg-D-Arg-D-Arg-Ad-D-Lys-NH$_2$

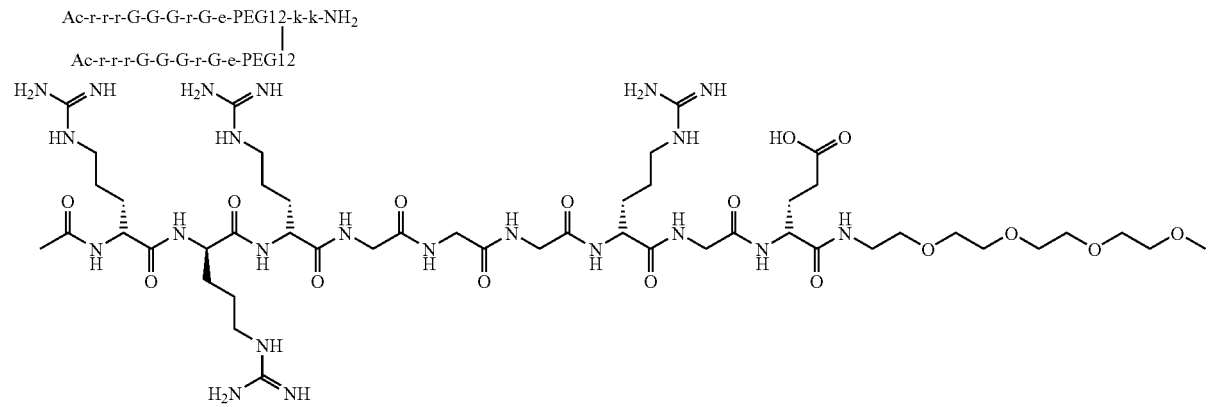

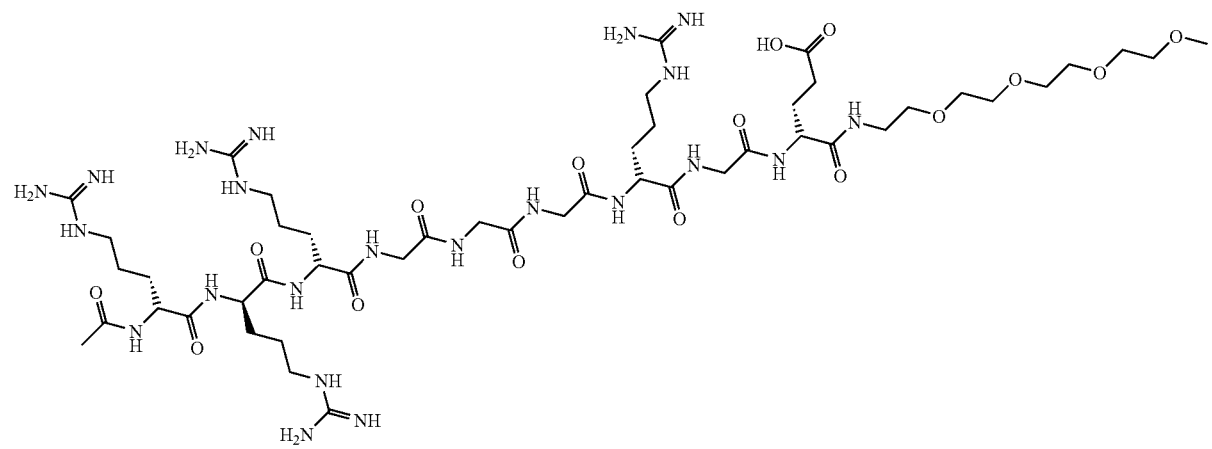

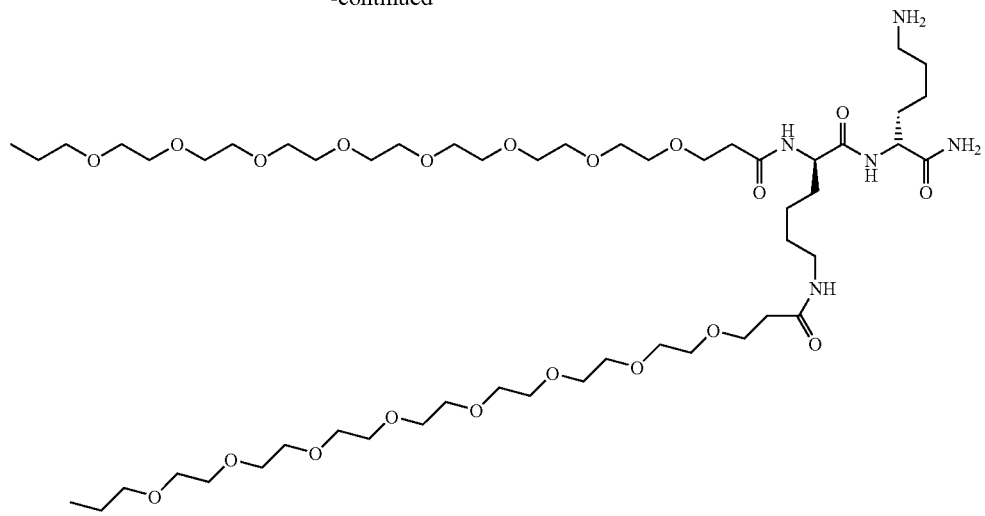

Assembly of the amino acid sequence D-Arg(Pbf)-D-Arg(Pbf)-D-Arg(Pbf)-Gly-Gly-Gly-D-Arg(Pbf)-Gly-D-Glu(Ot-Bu)-PEG12-D-Lys(-PEG12-D-Glu(Ot-Bu)-Gly-D-Arg(Pbf)-Gly-Gly-Gly-D-Arg(Pbf)-D-Arg(Pbf)-D-Arg(Pbf)-D-Lys(Boc) using fully automated synthesis (Liberty CEM microwave peptide synthesis) using NovaPEG Rink Amide resin (Novabiochem, 0.62 mmole/g; scale=0.05 mmole)=0.081 g). The amino acids (Iris Biotech and Novabiochem) were pre-activated using HBTU (Applied Biosystems) before coupling. The resin was acetylated using acetic anhydride (Merck, 10 eq.) and 4-methylmorpholine (Fluka, 20 eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried. Half of the crude product was purified using reverse phase preparative chromatography (Phenomenex Luna C18 column, 00G-4252-P0; solvents A=water/0.1% TFA and B=CH3CN/0.1% TFA; gradient 00-30% B over 40 min; flow 10 ml/minute; detection at 214 and 254 nm) affording 13.1 mg pure compound. Characterisation was done using analytical HPLC: Phenomenex Luna C18 column, 00G-4252-E0; solvents: A=water+0.1% TFA/B=CH$_3$CN+0.1% TFA, gradient: 10-45% B over 20 min; flow 1.0 ml/minute; retention time 8.8 minutes, detected at 214 and 254 nm). Further characterisation was carried out using mass spectrometry, giving m/z value 1761.8 [M-2H+].

Example 3

Synthesis of Ac-D-Arg-D-Pro-D-Arg-D-Pro-D-Arg-D-Pro-D-Arg-D-Pro-PEG4-D-Lys(PEG4-D-Pro-D-Arg-D-Pro-D-Arg-D-Pro-D-Arg-D-Pro-D-Arg-Ac)-D-Lys-NH$_2$ Ac-r-p-r-p-r-p-r-p-PEG4-k-k-NH$_2$
Ac-r-p-r-p-r-p-r-p-PEG4

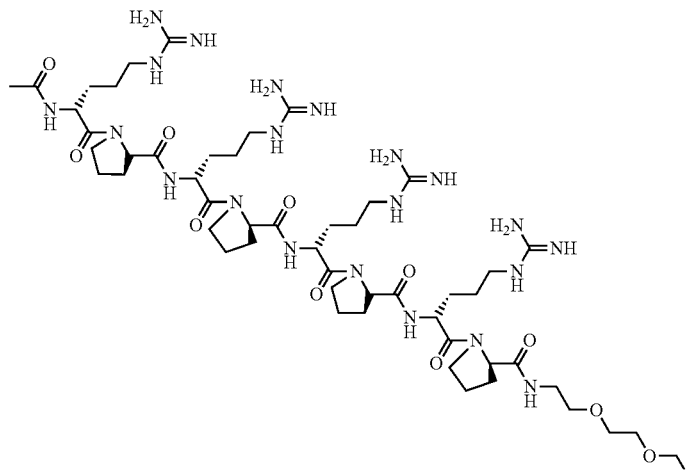

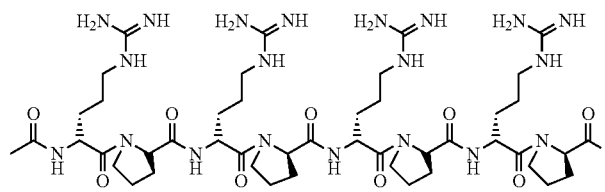 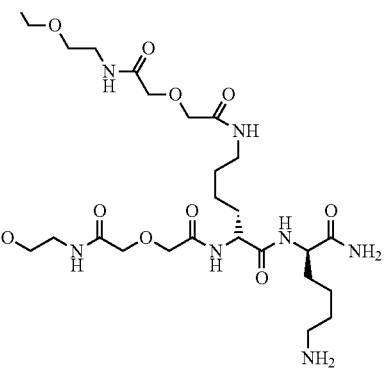

Assembly of the amino acid sequence (D-Arg(Pbf)-D-Pro-D-Arg(Pbf)-D-Pro-D-Arg(Pbf)-D-Pro-D-Arg(Pbf)-D-Pro-PEG4-D-Lys(PEG4-D-Pro-D-Arg(Pbf)-D-Pro-D-Arg(Pbf)-D-Pro-D-Arg(Pbf)-D-Pro-D-Arg(Pbf))-D-Lys(Boc) using fully automated synthesis (Liberty CEM microwave peptide synthesis) using NovaPEG Rink Amide resin (Novabiochem, 0.62 mmole/g; scale=0.05 mmole)=0.081 g). The amino acids (Iris Biotech and Novabiochem) were pre-activated using HBTU (Applied Biosystems) before coupling. The resin was acetylated using acetic anhydride (Merck, 10 eq.) and 4-methylmorpholine (Fluka, 20 eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried. Half of the crude product was purified using reverse phase preparative chromatography (Phenomenex Luna C18 column, 00G-4252-P0; solvents A=water/0.1% TFA and B=CH3CN/0.1% TEA; gradient 10-30% B over 40 min; flow 10 ml/minute; detection at 214 and 254 nm) affording 21.8 mg pure compound. Characterisation was done using analytical HPLC: Phenomenex Luna C18 column, 00G-4252-E0; solvents: A=water+0.1% TFA/B=CH$_3$CN+0.1% TFA, gradient: 10-25% B over 20 min; flow 1.0 ml/minute; retention time 9.6 minutes, detected at 214 and 254 nm). Further characterisation was carried out using mass spectrometry, giving m/z value 1824.4 [M-2H++3TFA].

Example 4

Synthesis of Ac-D-Arg-D-Arg-D-Arg-Gly-Gly-Gly-D-Arg-PEG12-D-Lys(PEG12-D-Arg-Gly-Gly-Gly-D-Arg-D-Arg-D-Arg-Ac)-k(Ac-D-Arg-D-Arg-D-Arg-Gly-Gly-Gly-D-Arg-PEG12-D-Lys(PEG12-D-Arg-Gly-Gly-Gly-D-Arg-D-Arg-D-Arg-Ac))-D-Lys-NH$_2$

```
Ac-r-r-r-G-G-G-r-PEG12
                      |
Ac-r-r-r-G-G-G-r-PEG12-k-k-k-N
                      |
Ac-r-r-r-G-G-G-r-PEG12-k
                      |
Ac-r-r-r-G-G-G-r-PEG12
```

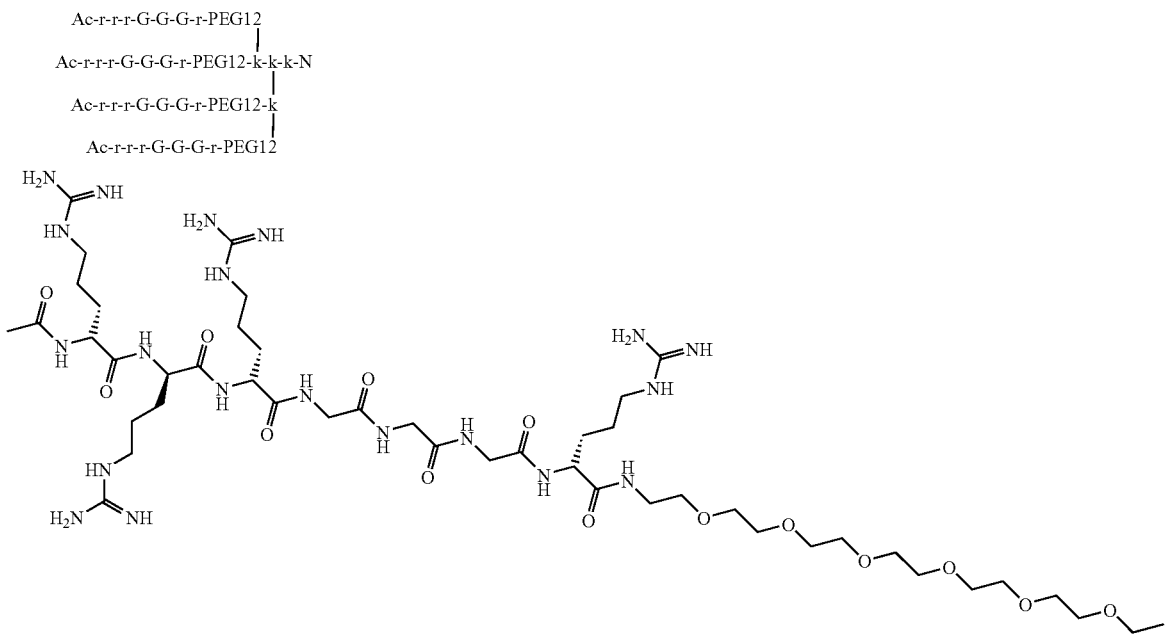

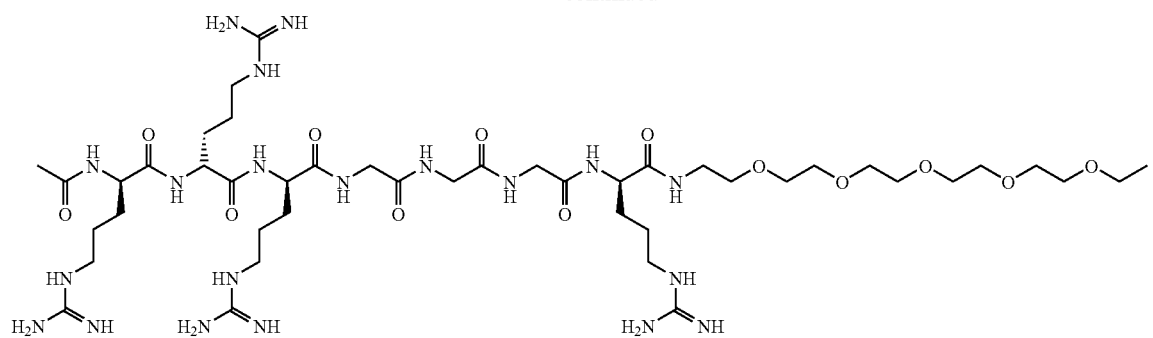
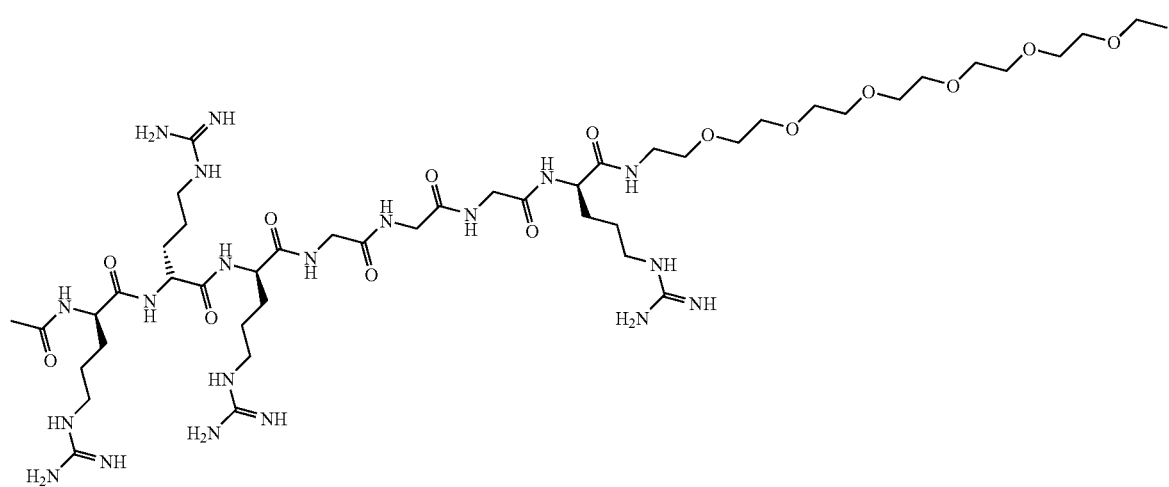
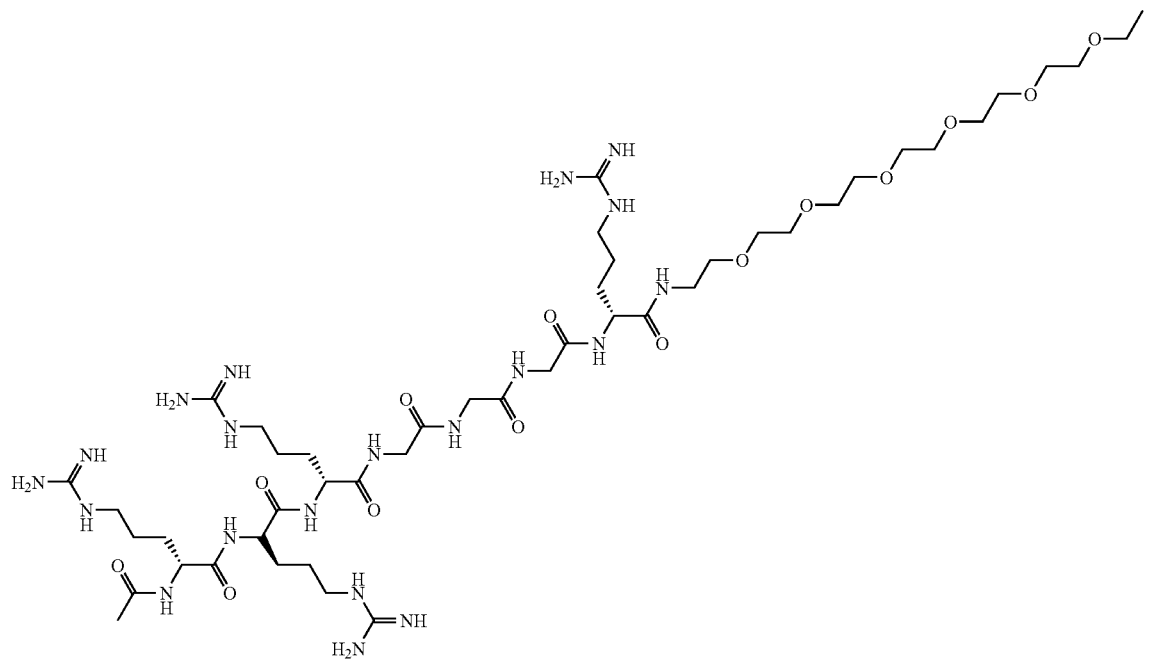

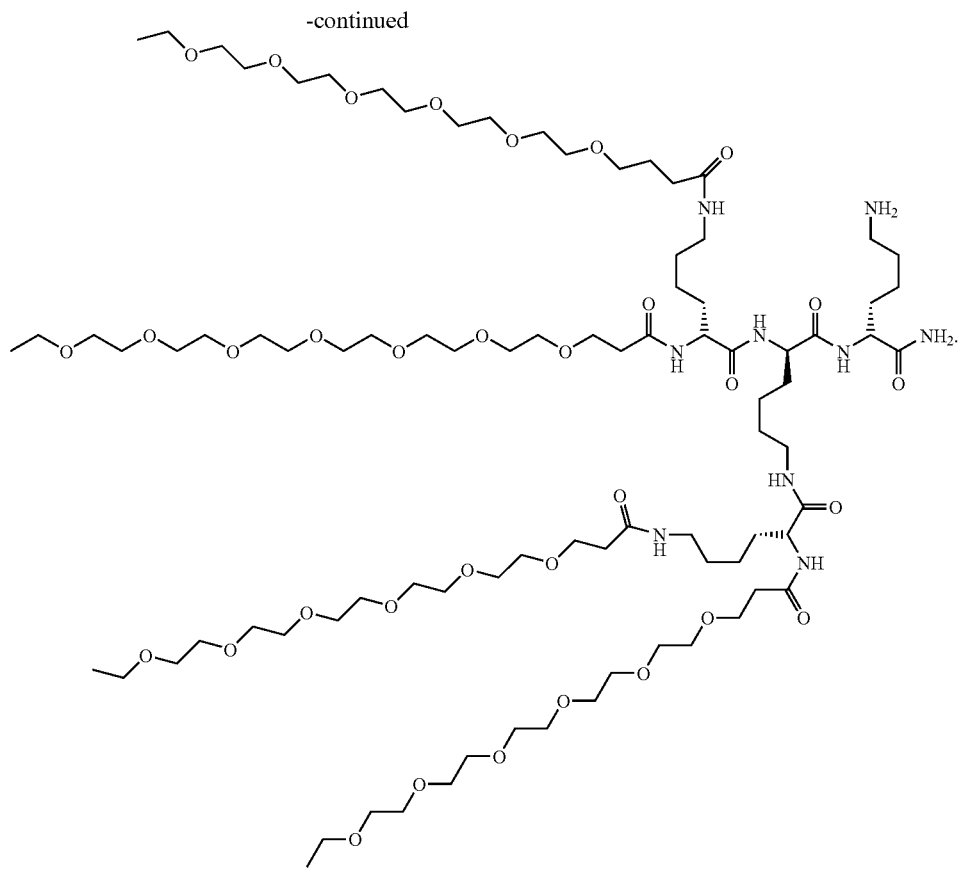

Assembly of the amino acid sequence (D-Arg(Pbf)-D-Arg(Pbf)-D-Arg(Pbf)-Gly-Gly-Gly-D-Arg(Pbf)-PEG12-D-Lys(PEG12-D-Arg(Pbf)-Gly-Gly-Gly-D-Arg(Pbf)-D-Arg(Pbf)-D-Arg(Pbf)-D-Lys(D-Arg(Pbf)-D-Arg(Pbf)-D-Arg(Pbf)-Gly-Gly-Gly-D-Arg(Pbf)-PEG12-D-Lys(PEG12-D-Arg(Pbf)-Gly-Gly-Gly-D-Arg(Pbf)-D-Arg(Pbf)-D-Arg(Pbf)))-D-Lys(Boc) using fully automated synthesis (Liberty CEM microwave peptide synthesis) using NovaPEG Rink Amide resin (Novabiochem, 0.62 mmole/g; scale=0.025 mmole)=0.040 g). The amino acids (Iris Biotech and Novabiochem) were pre-activated using HBTU (Applied Biosystems) before coupling. The resin to was acetylated using acetic anhydride (Merck, 10 eq.) and 4-methylmorpholine (Fluka, 20 eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried. ¼ of the crude product was purified using reverse phase preparative chromatography (Phenomenex Luna C18 column, 00G-4252-P0; solvents A=water/0.1% TFA and B=CH$_3$CN/0.1% TFA; gradient 00-30% B over 40 min; flow 10 ml/minute; detection at 214 and 254 nm) affording 2.8 mg pure compound. Characterisation was done using analytical HPLC: Phenomenex Luna C18 column, 00G-4252-E0; solvents: A=water+0.1% TFA/B=CH$_3$CN+0.1% TFA, gradient: 10-40% B over 20 min; flow 1.0 ml/minute; retention time 9.0 minutes, detected at 214 and 254 nm).

Example 5

Synthesis of Ac-D-Arg-D-Pro-D-Arg-D-Pro-D-Arg-D-Pro-D-Arg-D-Pro-PEG4 (PEG4-D-Pro-D-Arg-D-Pro-D-Arg-D-Pro-D-Arg-D-Pro-D-Arg-Ac)-k(Ac-D-Arg-D-Pro-D-Arg-D-Pro-D-Arg-D-Pro-D-Arg-D-Pro-PEG4-D-Lys(PEG4-D-Pro-D-Arg-D-Pro-D-Arg-D-Pro-D-Arg-D-Pro-D-Arg-Ad-D-Lys-NH$_2$

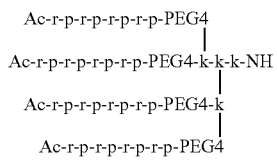

-continued
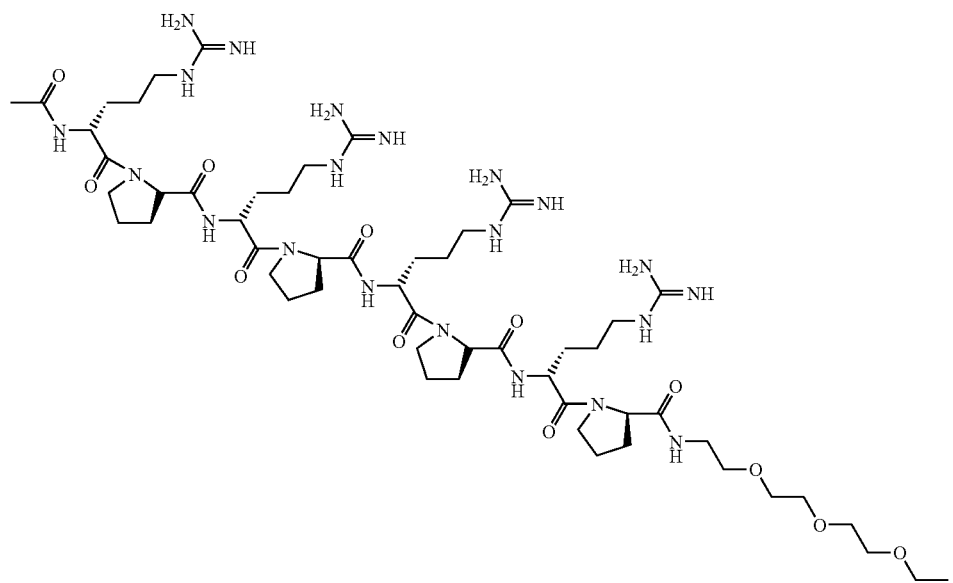
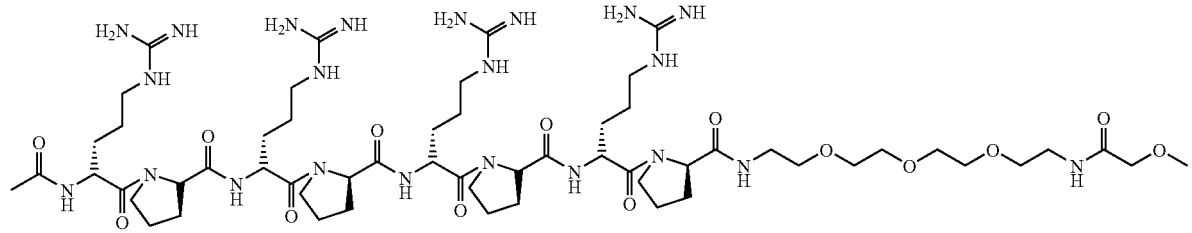
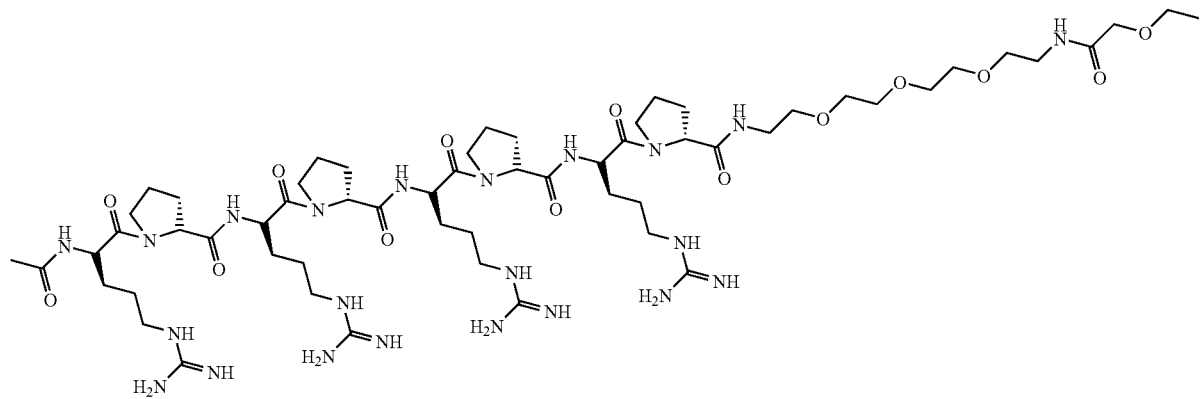

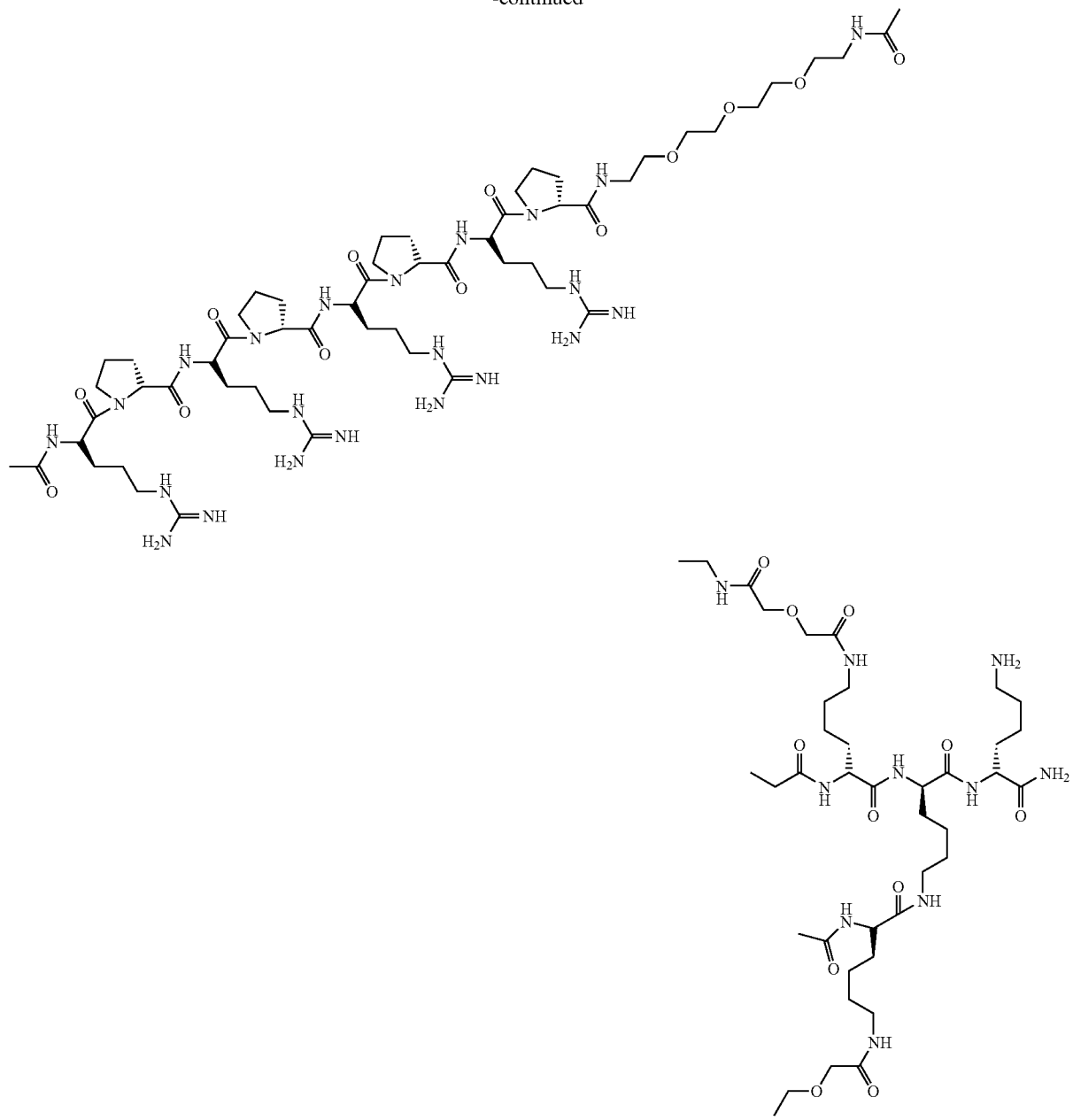

Assembly of the amino acid sequence (D-Arg(Pbf)-D-Pro-D-Arg(Pbf)-D-Pro-D-Arg(Pbf)-D-Pro-D-Arg(Pbf)-D-Pro-PEG4 (PEG4-D-Pro-D-Arg(Pbf)-D-Pro-D-Arg(Pbf)-D-Pro-D-Arg(Pbf)-D-Pro-D-Arg(Pbf)-D-Lys(D-Arg(Pbf)-D-Pro-D-Arg(Pbf)-D-Pro-D-Arg(Pbf)-D-Pro-D-Arg(Pbf)-D-Pro-PEG4-D-Lys(PEG4-D-Pro-D-Arg(Pbf)-D-Pro-D-Arg(Pbf)-D-Pro-D-Arg(Pbf)-D-Pro-D-Arg(Pbf)))-D-Lys(Boc)) using fully automated synthesis (Liberty CEM microwave peptide synthesis) using NovaPEG Rink Amide resin (Novabiochem, 0.62 mmole/g; scale=0.025 mmole)=0.040 g). The amino acids (Iris Biotech and Novabiochem) were pre-activated using HBTU (Applied Biosystems) before coupling. The resin was acetylated using acetic anhydride (Merck, 10 eq.) and 4-methylmorpholine (Fluka, 20 eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried. Half of the crude product was purified using reverse phase preparative chromatography (Phenomenex Luna C18 column, 00G-4252-P0; solvents A=water/0.1% TFA and B=CH$_3$CN/0.1% TFA; gradient 00-30% B over 40 min; flow 10 ml/minute; detection at 214 and 254 nm) affording 6.8 mg pure compound. Characterisation was done using analytical HPLC: Phenomenex Luna C18 column, 00G-4252-E0; solvents: A=water+0.1% TFA is/B=CH$_3$CN+0.1% TFA, gradient: 10-25% B over 20 min; flow 1.0 ml/minute; retention time 10.5 minutes, detected at 214 and 254 nm).

Example 6
Synthesis of Ac-D-Arg-D-Lys-D-Lys-D-Arg-D-Arg-D-Orn-D-Arg-D-Arg-D-Arg-Gly-D-Glu-D-Glu-PEG12-D-Lys(PEG12-D-Glu-D-Glu-D-Gly-D-Arg-D-Arg-D-Arg-D-Orn-D-Arg-D-Arg-D-Lys-D-Lys-D-Arg-Ac)-D-Cys-NH₂
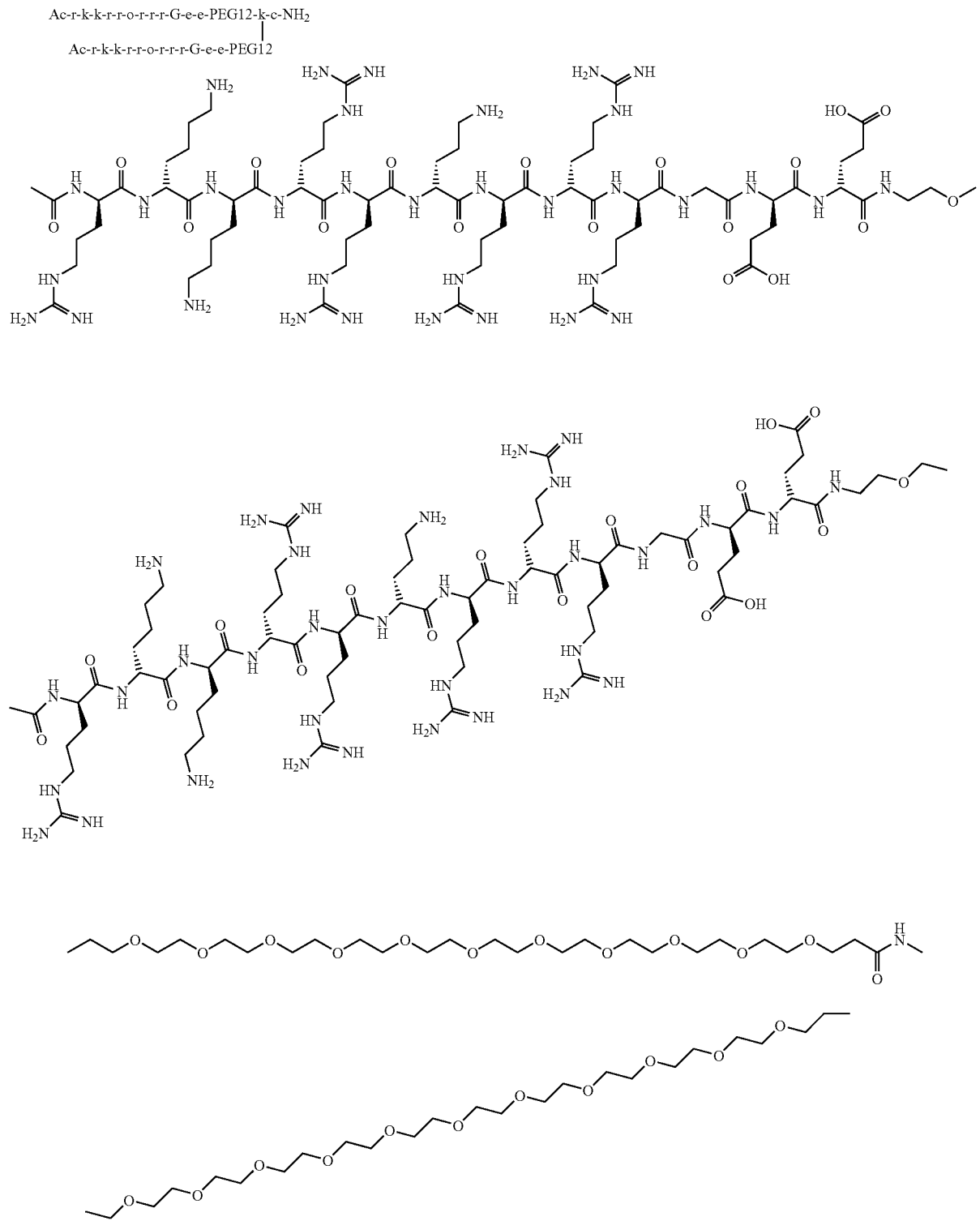

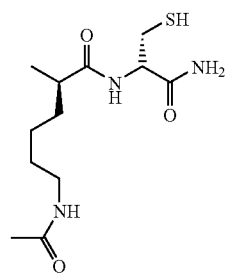

Assembly of the amino acid sequence D-Arg(Pbf)-D-Lys(Boc)-D-Lys(Boc)-D-Arg(Pbf)-D-Arg(Pbf)-D-Orn(Boc)-D-Arg(Pbf)-D-Arg(Pbf)-D-Arg(Pbf)-Gly-D-Glu(OtBu)-D-Glu(OtBu)-PEG12-D-Lys(PEG12-D-Glu(OtBu)-D-Glu(OtBu)-Gly-D-Arg(Pbf)-D-Arg(Pbf)-D-Arg(Pbf)-D-Orn(Boc)-D-Arg(Pbf)-D-Arg(Pbf)-D-Lys(Boc)-D-Lys(Boc)-D-Arg(Pbf))-D-Cys(Trt) was assembled on a CEM Liberty microwave peptide synthesiser using Fmoc chemistry starting with 0.05 mmol NovaPEG Rink Amide resin (Novabiochem). An amount of 0.4 mmol amino acid (Iris Biotech, Fluka and Novabiochem) was applied in each coupling step using HATU (GenScript Corp.), HOAt (GenScript Corp.) and DIEA (Fluka) for in situ activation. The resin was acetylated using acetic anhydride (Merck, 10 eq.) and DIEA (Fluka, 11. eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried. Half of the crude product was purified using reverse phase preparative chromatography (Phenomenex Luna C18 column, 00G-4252-P0; solvents A=water/0.1% TFA and B=$CH_3CN$/0.1% TFA; gradient 10-50% B over 40 min; flow 10 ml/minute; detection at 214 and 254 nm) affording the pure compound. Characterisation was done using analytical HPLC: Phenomenex Luna 3μ C18 (2) 20×2 mm; solvents: A=water+0.1% TFA/B=$CH_3CN$+0.1% TFA, gradient: 10-50% B over 5 min; flow 0.6 ml/minute; retention time 1.77 minutes, detected at 214 nm). Further characterisation was carried out using mass spectrometry, giving m/z value 1593.3 [$M3H^{3+}$].

Example 7

Synthesis of Ac-D-Arg-D-Lys-D-Lys-D-Arg-D-Arg-D-Orn-D-Arg-D-Arg-D-Arg-PEG12-D-Lys(PEG12-D-D-Arg-D-Arg-D-Arg-D-Orn-D-Arg-D-Arg-D-Lys-D-Lys-D-Ara-Ac)-D-Cys-$NH_2$

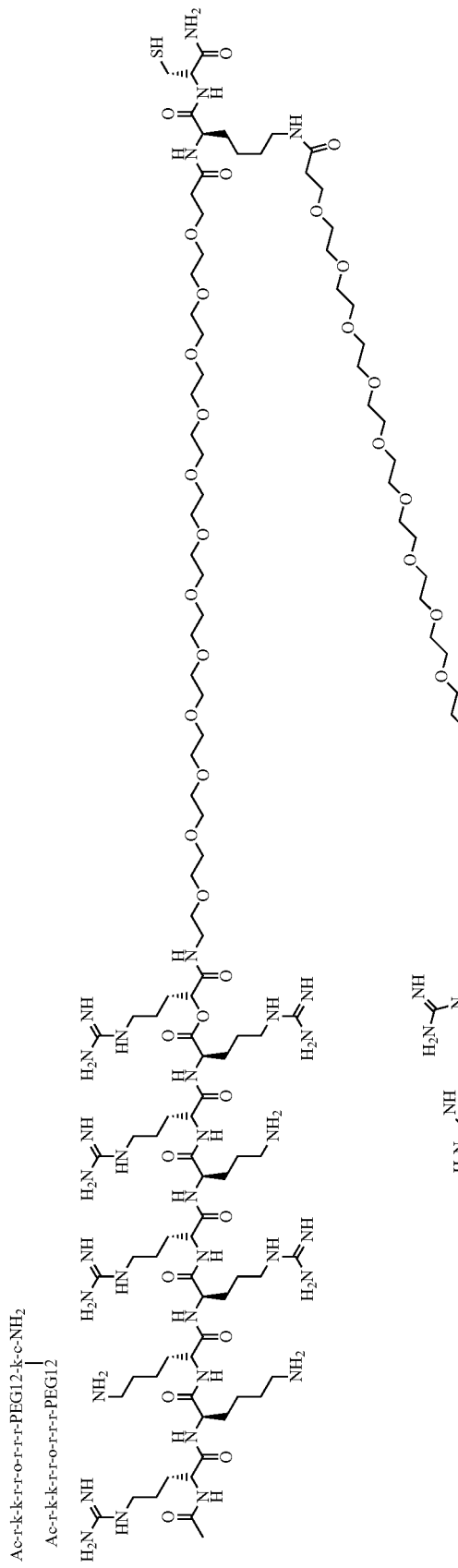
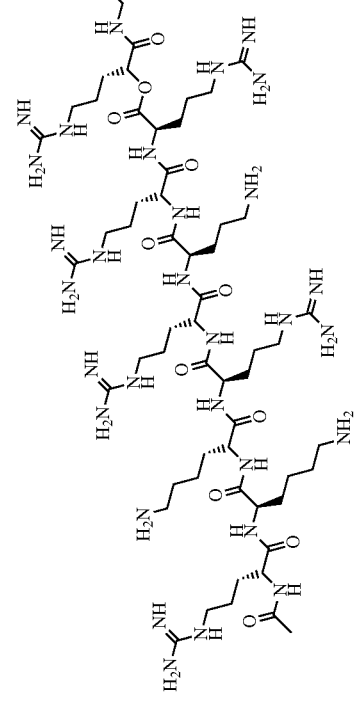

Assembly of the amino acid sequence D-Arg(Pbf)-D-Lys(Boc)-D-Lys(Boc)-D-Arg(Pbf)-D-Arg(Pbf)-D-Orn(Boc)-D-Arg(Pbf)-D-Arg(Pbf)-D-Arg(Pbf)-PEG12-D-Lys(PEG12-D-D-Arg(Pbf)-D-Arg(Pbf)-D-Arg(Pbf)-D-Orn(Boc)-D-Arg(Pbf)-D-Arg(Pbf)-D-Lys(Boc)-D-Lys(Boc)-D-Arg(Pbf))-D-Cys(Trt) was assembled on a CEM Liberty microwave peptide synthesiser using Fmoc chemistry starting with 0.05 mmol NovaPEG Rink Amide resin (Novabiochem). An amount of 0.4 mmol amino acid (Iris Biotech, Fluka and Novabiochem) was applied in each coupling step using HATU (GenScript Corp.), HOAt (GenScript Corp.) and DIEA (Fluka) for in situ activation. The resin was acetylated using acetic anhydride (Merck, 10 eq.) and DIEA (Fluka, 11 eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried.

Half of the crude product was purified using reverse phase preparative chromatography (Phenomenex Luna C18 column, 00G-4252-P0; solvents A=water/0.1% TFA and B=$CH_3CN$/0.1% TFA; gradient 10-35% B over 40 min; flow 10 ml/minute; detection at 214 and 254 nm) affording the pure compound. Characterisation was done using analytical HPLC: Phenomenex Luna 3μ C18 (2) 20×2 mm; solvents: A=water+0.1% TFA/B=CH3CN+0.1% TFA, gradient: 10-30% B over 5 min; flow 0.6 ml/minute; retention time 2.80 minutes, detected at 214 nm). Further characterisation was carried out using mass spectrometry, giving m/z value 1265.3 [(M4H+8TFA)$^{4+}$].

Example 8

Synthesis of Ac-D-Arg-D-Arg-D-Ara-Gly-Gly-D-Arg-D-Arg-D-Ara-Gly-Gly-D-Arg-D-Ara-PEG12-D-Lys(PEG12-D-Arg-D-Ara-Gly-Gly-D-Arg-D-Arg-D-Ara-Gly-Gly-D-Arg-D-Arg-D-Arq-Ac)-D-Lys-$NH_2$

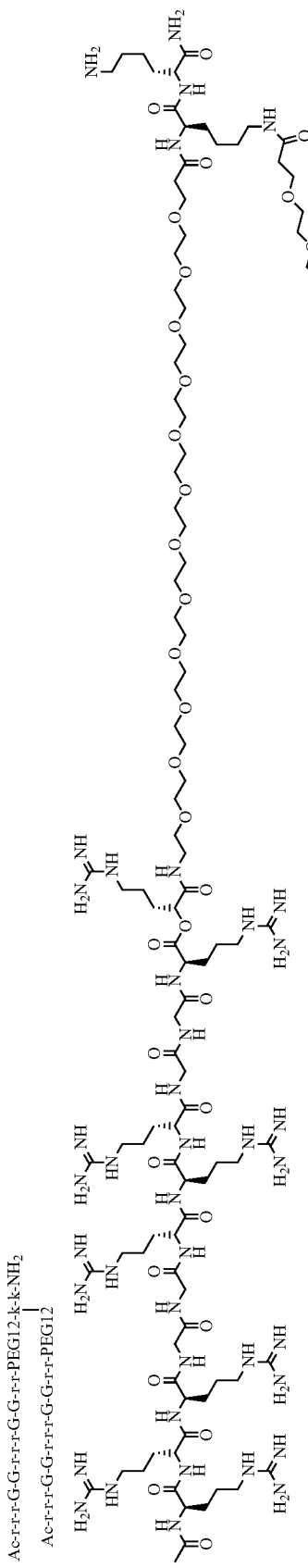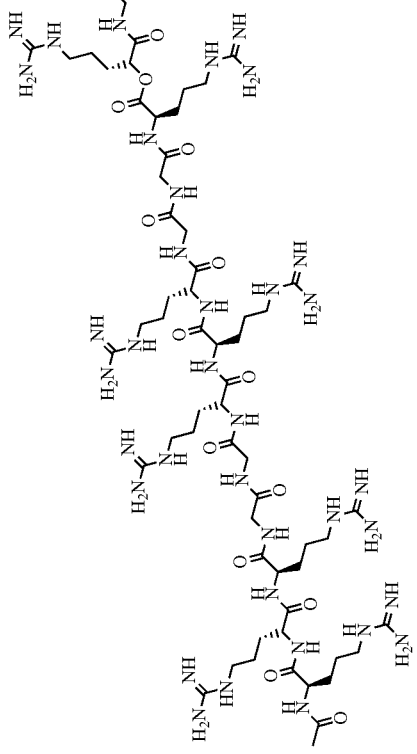

Assembly of the amino acid sequence D-Arg(Pbf)-D-Arg(Pbf)-D-Arg(Pbf)-Gly-Gly-D-Arg(Pbf)-D-Arg(Pbf)-D-Arg(Pbf)-Gly-Gly-D-Arg(Pbf)-D-Arg(Pbf)-PEG12-D-Lys(PEG12-D-Arg(Pbf)-D-Arg(Pbf)-Gly-Gly-D-Arg(Pbf)-D-Arg(Pbf)-D-Arg(Pbf)-Gly-Gly-D-Arg(Pbf)-D-Arg(Pbf)-D-Arg(Pbf)-D-Lys(Boc) was assembled on a CEM Liberty microwave peptide synthesiser using Fmoc chemistry starting with 0.05 mmol NovaPEG Rink Amide resin (Novabiochem). An amount of 0.4 mmol amino acid (Iris Biotech, Fluka and Novabiochem) was applied in each coupling step using HATU (GenScript Corp.), HOAt (GenScript Corp.) and DIEA (Fluka) for in situ activation. The resin was acetylated using acetic anhydride (Merck, 10 eq.) and DIEA (Fluka, 11 eq.) in dimethylformamide (Rathburn). The simultaneous removal of side-chain protecting groups and peptide from the resin was carried out in trifluoroacetic acid (Fluka) containing 2.5% water and 2.5% triisopropylsilane (Aldrich) over night. The resin was removed by filtration and the filtrate evaporated in vacuo. Diethyl ether (Eternell) was added to the residue. The resulting precipitate was washed with ether and air-dried.

Half of the crude product was purified using reverse phase preparative chromatography (Phenomenex Luna C18 column, 00G-4252-P0; solvents A=water/0.1% TFA and B=CH$_3$CN/0.1% TFA; gradient 10-35% B over 40 min; flow 10 ml/minute; detection at 214 and 254 nm) affording the pure compound. Characterisation was done using analytical HPLC: Phenomenex Luna 3μ C18 (2) 20×2 mm; solvents: A=water+0.1% TFA/B=CH$_3$CN+0.1% TFA, gradient: 10-30% B over 5 min; flow 0.6 ml/minute; retention time 2.19 minutes, detected at 214 nm). Further characterisation was carried out using mass spectrometry, giving m/z value 808.5 [(M6H+3TFA)$^{6+}$].

Example 9

Synthesis of Ac-D-Arg-D-Arg-D-Ara-Gly-Gly-Gly-D-Ara-PEG12-D-Lys(-PEG12-D-Arg-Gly-Gly-Gly-D-Arg-D-Arg-D-Arg-Ac)-D-Lys(COCH$_2$NH-His-OH)—NH$_2$ and its $^{99m}$Tc complex

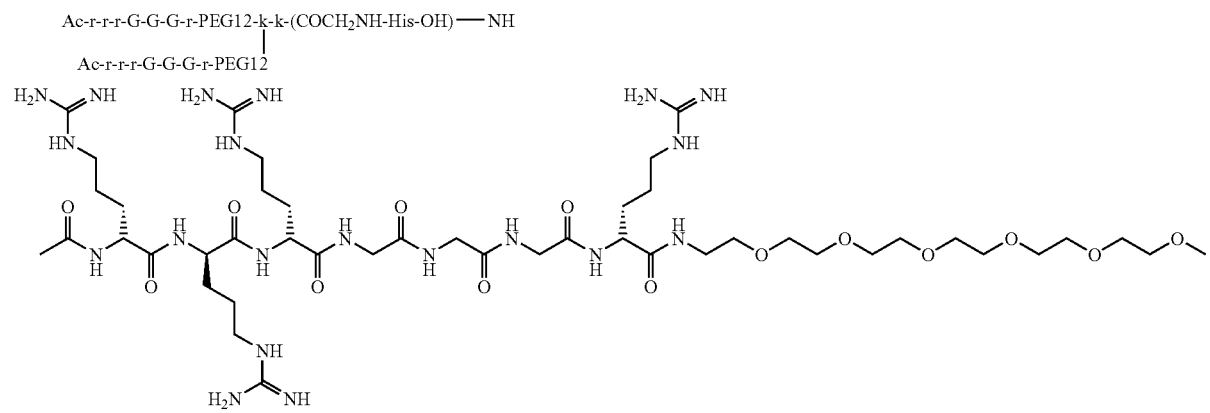

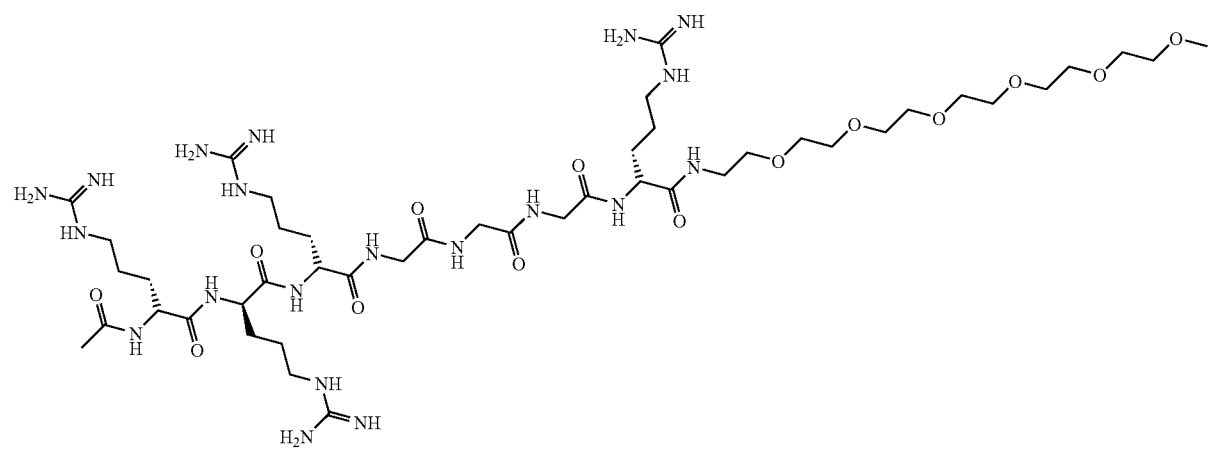

-continued

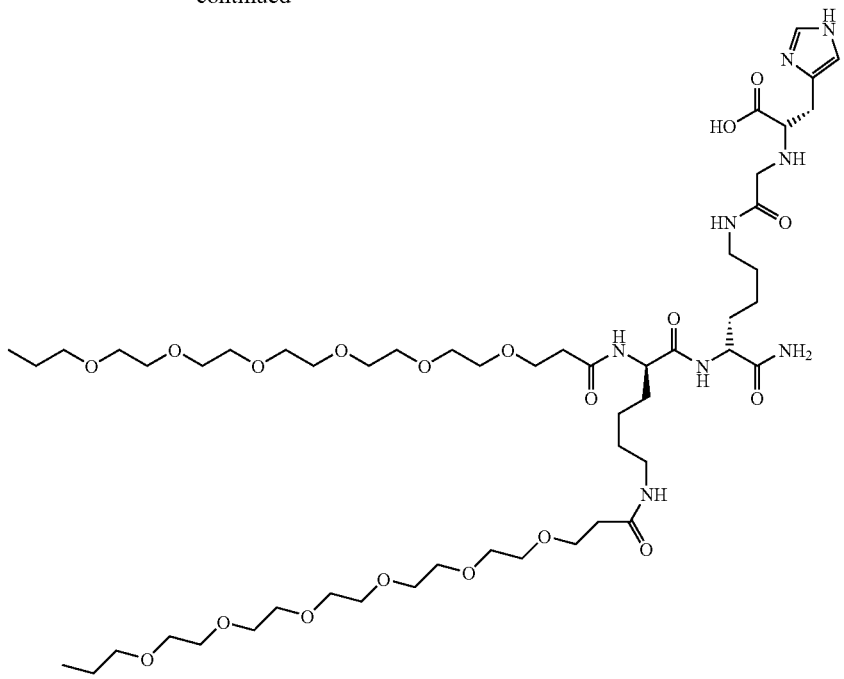

(S)-2(tert-Butoxycarbonyl-carboxymethyl-amino)-3-(1-trityl-1H-imidazol-4-yl)-propionic acid tert-butyl ester (1.0 mg, 1.6 μmole), PyAOP (Applied Biosystems, 0.86 mg, 1.6 μmole) and diisopropyl ethyl amine (Fluka, 0.55 μL, 3.2 μmole) in dimethylformamide (Rathburn, 0.6 mL) was added peptide from Example 1 (3.4 mg, 1.1 μmole). The solution was left over night before the crude product (with dimethylformamide) was purified by reverse phase preparative chromatography (Phenomenex Luna C18 column, 00G-4252-P0; solvents A=water/0.1% TFA and B=CH3CN/0.1% TFA; gradient 10-40% B over 40 min; flow 10 ml/minute; detection at 214 and 254 nm). Characterisation was carried out using mass spectrometry, giving m/z value 1438.0 [M-3H++5TFA]. The protecting groups on the chelate were removed using trifluoroacetic acid (Fluka) (95%), water (2.5%) and triisopropylsilane (Aldrich) (2.5%). TFA was evaporated under reduced pressure after one hour and the crude product purified using reverse phase preparative chromatography (Phenomenex Luna C18 column, 00G-4252-N0; solvents A=water/0.1% HCOOH and B=CH₃CN/0.1% HCOOH; gradient 00-20% B over 30 min; flow 5 ml/minute; detection at 214 and 254 nm) affording 1.5 mg pure compound. Characterisation was done using analytical HPLC: Phenomenex Luna C18 column, 00G-4252-E0; solvents: A=water+0.1% TFA/B=CH3CN+0.1% TFA, gradient: 10-40% B over 20 min; flow 1.0 ml/minute; retention time 8.7 minutes, detected at 214 and 254 nm). Further characterisation was carried out using mass spectrometry, giving m/z value 1672.3 [M-2H+].

The hereby obtained product of the formula Ac-D-Arg-D-Arg-D-Arg-Gly-Gly-Gly-D-Arg-PEG12-D-Lys(-PEG12-D-Arg-Gly-Gly-Gly-D-Arg-D-Arg-D-Arg-Ac)-D-Lys (COCH₂NH-His-OH)—NH₂ is coordinated with 99mTc through the carboxylic acid group and the imidazole.

Example 10

Synthesis of Ac-D-Arg-D-Arg-D-Arg-Gly-Gly-Gly-D-Arg-PEG12-D-Lys(—PEG12-D-Arg-Gly-Gly-Gly-D-Arg-D-Arg-D-Arg-Ac)-D-Lys(COCH₂CH(CH₂NHCH₂CH₂NH₂)₂)—NH₂ and its $^{99m}$Tc complex

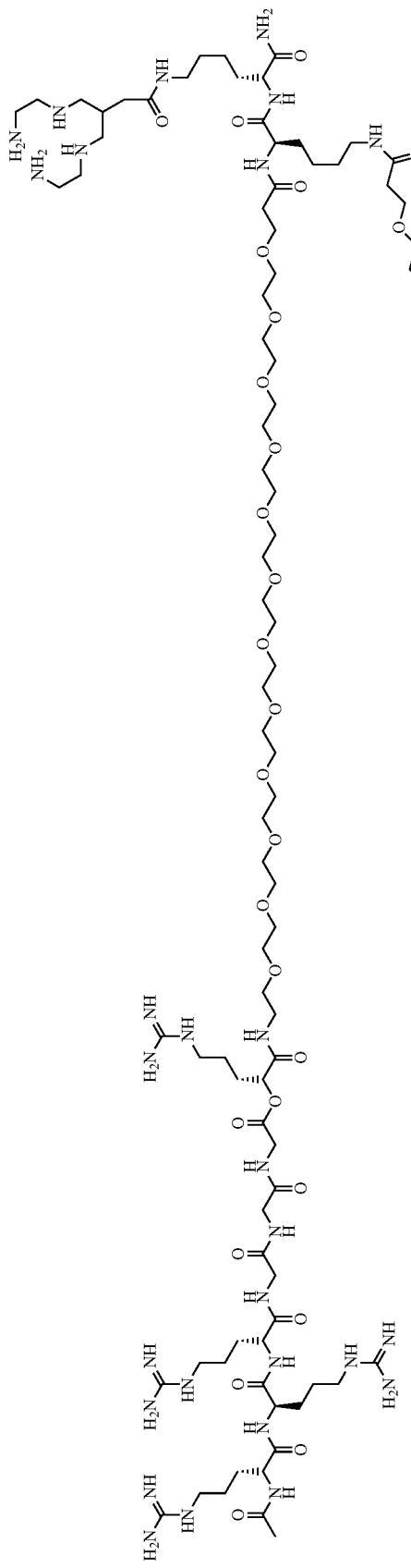
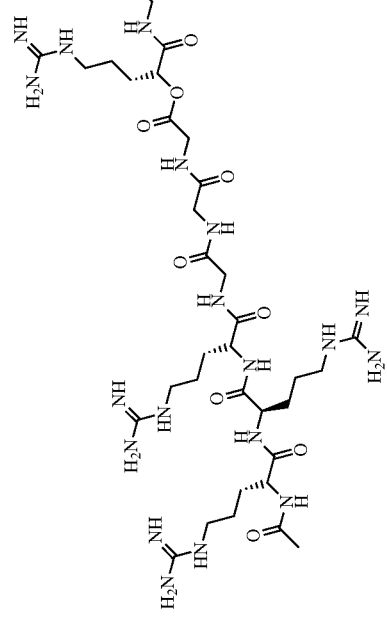
Ac-r-r-r-G-G-G-r-PEG12-k-k(COCH₂CH(CH₂NHCH₂CH₂NH₂)₂)—NH₂
|
Ac-r-r-r-G-G-G-r-PEG12

N-Succinimidyl 4-(2-amino-ethylamino)-3-[(2-amino-ethylamino)-methyl]-butyrate (1.2 mg, 1.6 μmole), HOAt (Genscript Corp., 0.20 mg, 1.6 μmole) and diisopropyl ethyl amine (Fluka, 0.55 μL, 3.2 μmole) in dimethylformamide (Rathburn, 0.6 mL) was added peptide from Example 1 (3.4 mg, 1.1 μmole). The solution was left over night before the crude product (with dimethylformamide) was purified by reverse phase preparative chromatography (Phenomenex Luna C18 column, 00G-4252-P0; solvents A=water/0.1% TFA and B=CH₃CN/0.1% TFA; gradient 10-50% B over 40 min; flow 10 ml/minute; detection at 214 and 254 nm). Characterisation was carried out using mass spectrometry, giving m/z value 1440.2 [M-3H++5TFA]. The protecting groups on the chelate were removed using trifluoroacetic acid (Fluka) (97.5%) and water (2.5%). TFA was evaporated under reduced pressure after one hour and the crude product was purified using reverse phase preparative chromatography (Phenomenex Luna C18 column, 00G-4252-P0; solvents A=water/0.1% TFA and B=CH₃CN/0.1% TFA; gradient 10-40% B over 40 min; flow 10 ml/minute; detection at 214 and 254 nm) affording 1.9 mg pure compound. Characterisation was done using analytical HPLC: Phenomenex Luna C18 column, 00G-4252-E0; solvents: A=water+0.1% TFA/B=CH₃CN+0.1% TFA, gradient: 10-40% B over 20 min; flow 1.0 ml/minute; retention time 8.5 minutes, detected at 214 and 254 nm). Further characterisation was carried out using mass spectrometry, giving m/z value 1674.8 [M-2H+].

A radioactive imaging entity, preferably $^{99m}$Tc, can be added using known methodology, e.g. from WO 03/006070

Example 11

Synthesis of Ac-D-Arg-D-Arg-D-Arg-Gly-Gly-Gly-D-Ara-PEG12-D-Lys(—PEG12-D-Arg-Gly-Gly-Gly-D-Arg-D-Arg-D-Ara-Arg-D-Lys((3-[4-hydroxy-phenyl)propionyl]-NH₂ and its iodinated derivative

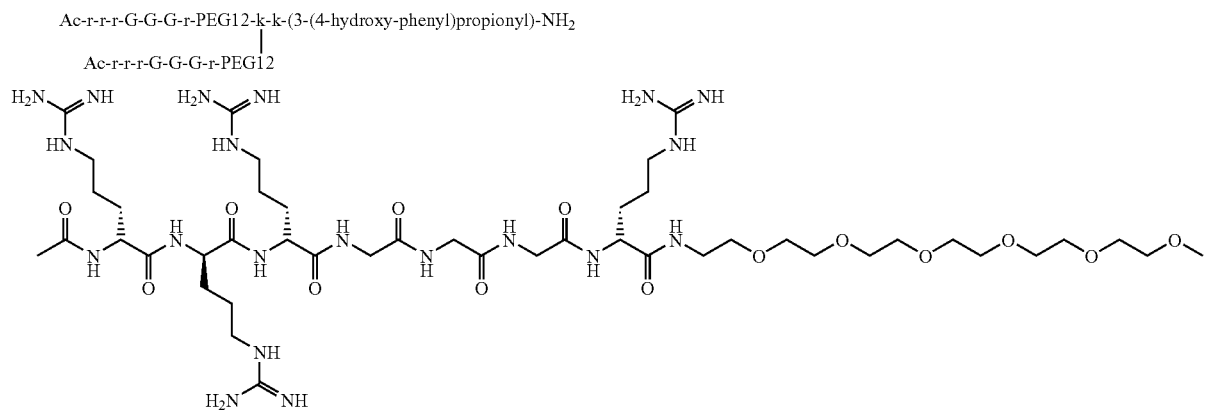

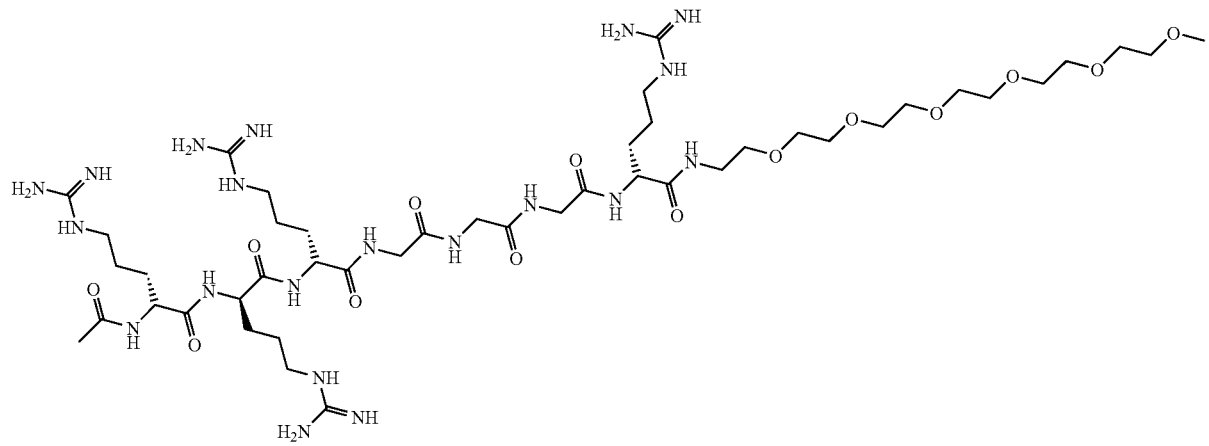

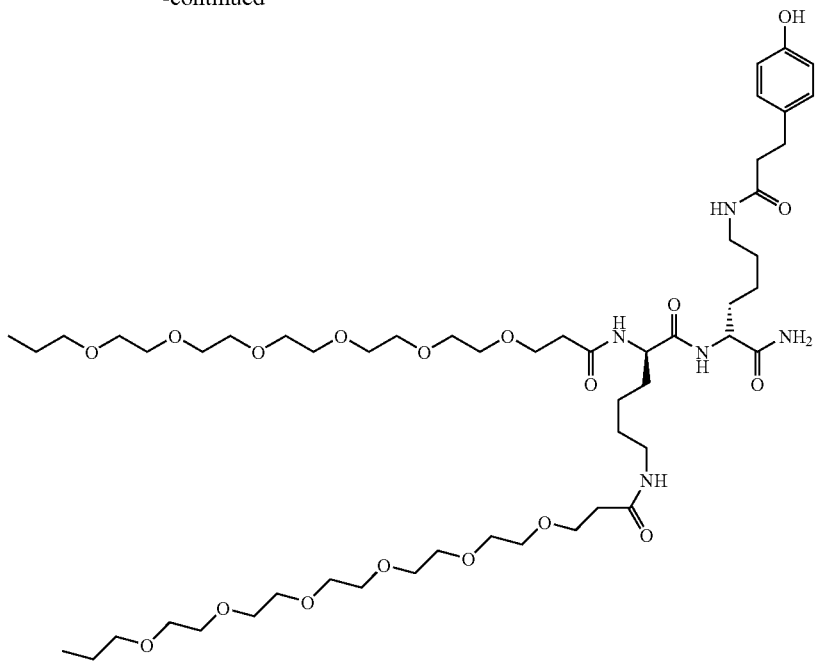

3-(4-Hydroxyphenyl)propionic acid N-hydroxysuccinimide ester (Sigma, 0.40 mg, 1.6 μmole) and diisopropyl ethyl amine (Fluka, 0.55 μL, 3.2 μmole) in dimethylformamide (Rathburn, 0.6 mL) was added peptide from Example 1 (3.4 mg, 1.1 μmole). The solution was left over night before the crude product (with dimethylformamide) was purified using reverse phase preparative chromatography (Phenomenex Luna C18 column, 00G-4252-P0; solvents A=water/0.1% TFA and B=CH$_3$CN/0.1% TFA; gradient 10-50% B over 40 min; flow 10 ml/minute; detection at 214 and 254 nm) affording 2.0 mg pure compound. Characterisation was done using analytical HPLC: Phenomenex Luna C18 column, 00G-4252-E0; solvents: A=water+0.1% TFA/B=CH$_3$CN+0.1% TFA, gradient: 10-40% B over 20 min; flow 1.0 ml/minute; retention time 9.7 minutes, detected at 214 and 254 nm). Further characterisation was carried out using mass spectrometry, giving m/z value 1289.4 [M-3H++5TFA].

Iodinated Derivative:

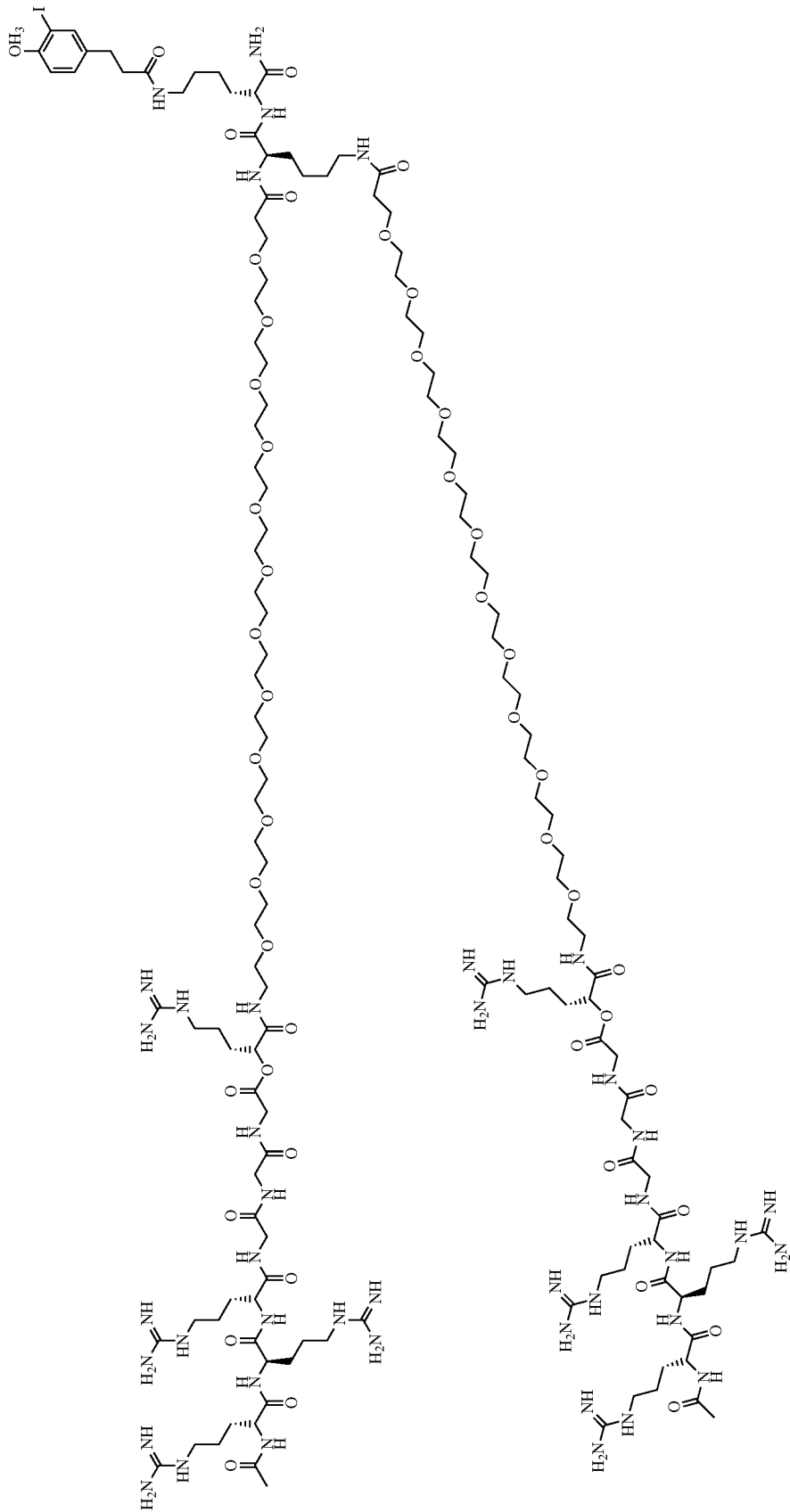

To prepare the iodinated derivative, the method described by Bolton [J. Lab. Comp. Radiopharm., 45, 485-528 (2002)] can be employed to introduce an iodine atom in the ortho position of the phenolic group.
Example 12
Synthesis of Ac-D-Arg-D-Arg-D-Arg-Gly-Gly-Gly-D-Arg-PEG12-D-Lys(-PEG12-D-Arg-Gly-Gly-Gly-D-Arg-D-Arg-D-Arg-Ac)-D-Lys(Cy5.5)-NH$_2$
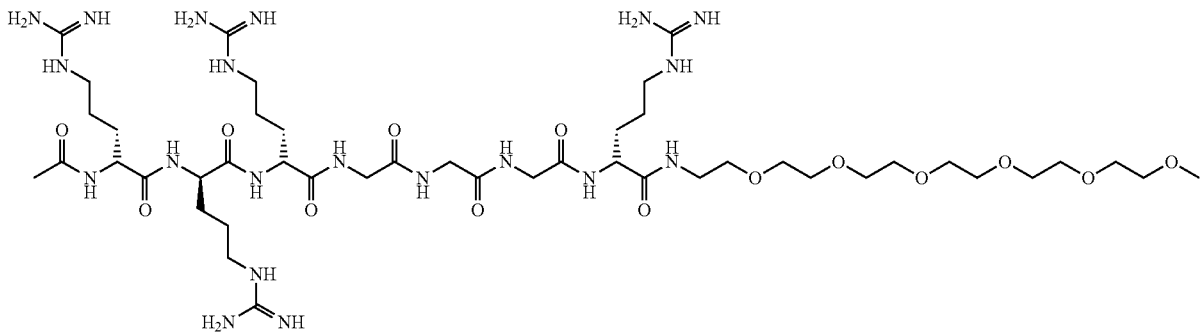
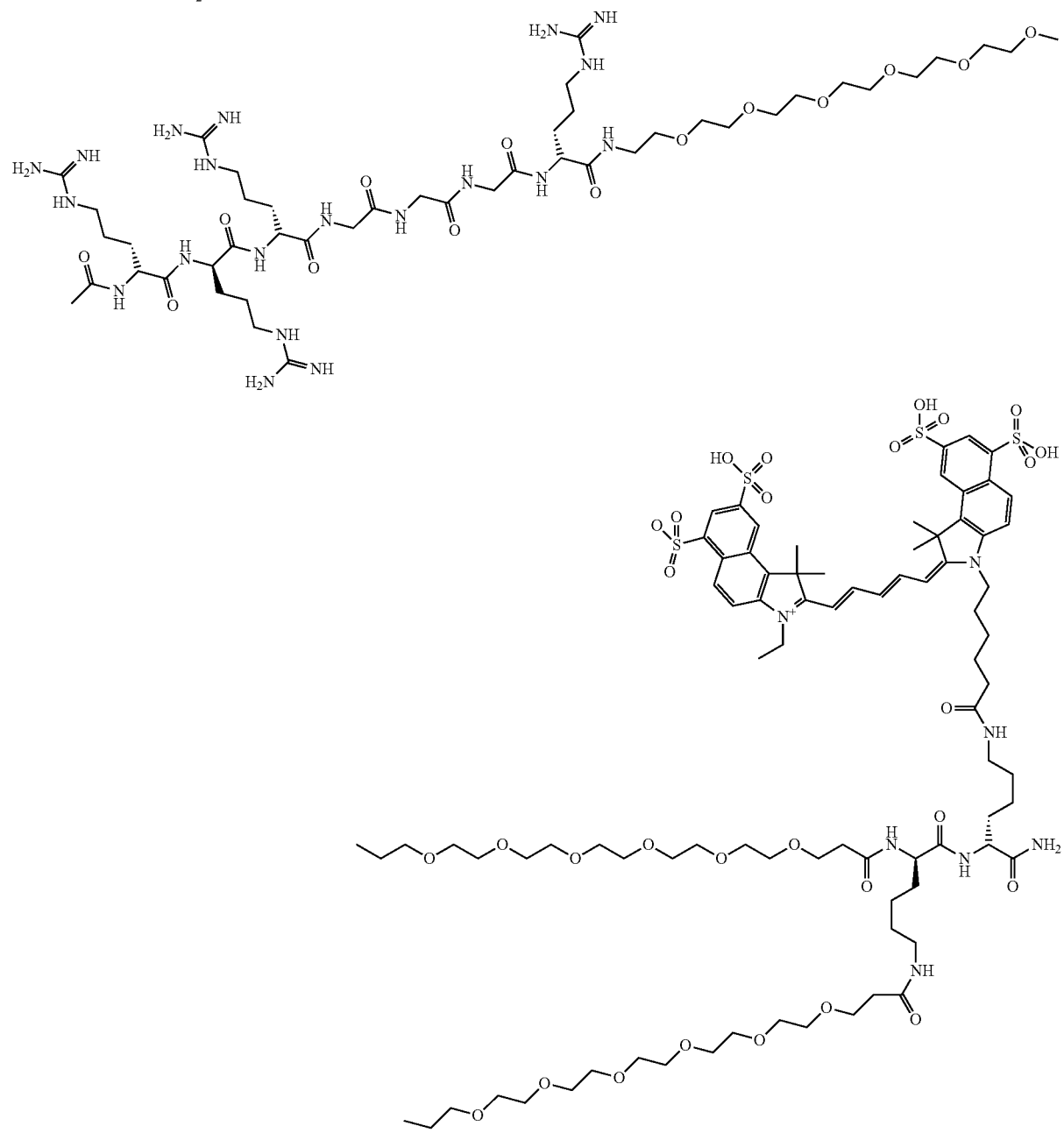

A solution of Cy5.5 NHS ester (GE Healthcare, 1.5 mg, 1.3 μmoles) and sym.-collidine (Fluka, 1.2 μL, 9.1 μmoles) dissolved in N-methylpyrrolidone (Applied biosystems, 0.25 mL) was added peptide from Example 1 (2.8 mg, 0.89 μmoles) dissolved in dimethylformamide (Rathburn, 0.25 mL) and the clear blue reaction mixture was protected from light and stirred over night. The reaction mixture was then diluted with water/0.1% TFA (6 mL) and the product purified using preparative HPLC affording reverse phase preparative chromatography (Phenomenex Luna C18 column, 00G-4252-P0; solvents A=water/0.1% TFA and B=CH$_3$CN/0.1% TFA; gradient 00-40% B over 40 min; flow 10 ml/minute; detection at 214 and 254 nm) affording 1.1 mg pure compound. Characterisation was done using analytical HPLC: Phenomenex Luna C18 column, 00G-4252-E0; solvents: A=water+0.1% TFA/B=CH$_3$CN+0.1% TFA, gradient: 10-25% B over 20 min; flow 1.0 ml/minute; retention time 16.5 minutes, detected at 214 and 254 nm). Further characterisation was carried out using mass spectrometry, giving m/z value 1350.4 [M-3H+].

Example 13

Synthesis of Ac-D-Arg-D-Arg-D-Arg-Gly-Gly-Gly-D-Arg-PEG12-D-Lys(—PEG12-D-Arg-Gly-Gly-Gly-D-Arg-D-Arg-D-Arg-Ac)-D-Lys(Cy5**)—NH$_2$

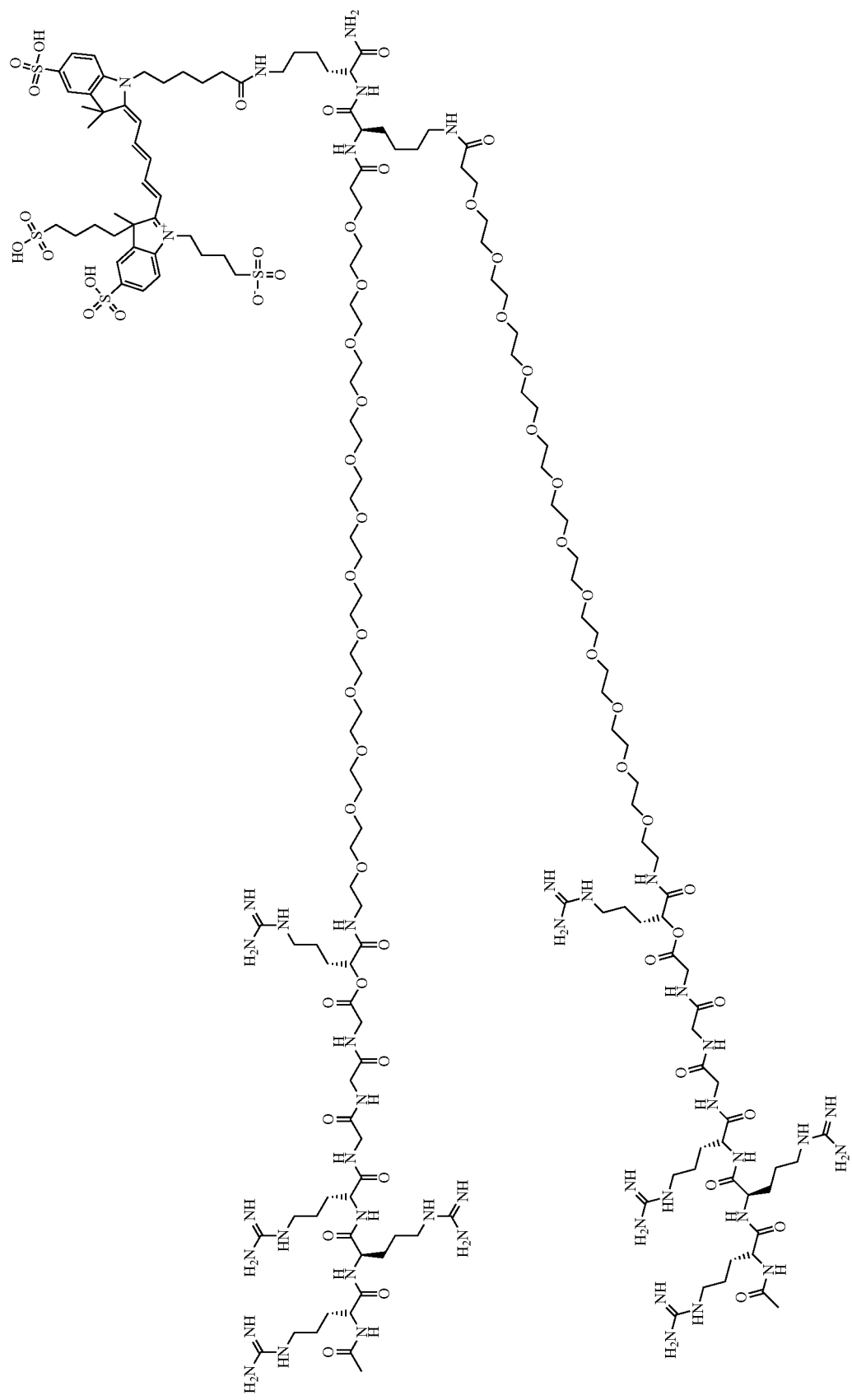

A solution of Cy5** NHS ester (GE Healthcare, 1.8 mg, 1.3 μmoles) and sym.-collidine (Fluka, 1.2 μL, 9.1 μmoles) dissolved in N-methylpyrrolidone (Applied biosystems, 0.25 mL) was added peptide from Example 1 (2.8 mg, 0.89 μmoles) dissolved in dimethylformamide (Rathburn, 0.25 mL) and the clear blue reaction mixture was protected from light and stirred over night. The reaction mixture was then diluted with water/0.1% TFA (6 mL) and the product purified using reverse phase preparative chromatography (Phenomenex Luna C18 column, 00G-4252-PO; solvents A=water/ 0.1% TFA and B=$CH_3CN$/0.1% TFA; gradient 10-40% B over 40 min; flow 10 ml/minute; detection at 214 and 254 nm) affording 1.2 mg pure compound. Characterisation was done using analytical HPLC: Phenomenex Luna C18 column, 00G-4252-E0; solvents: A=water+0.1% TFA/B=$CH_3CN$+ 0.1% TFA, gradient: 10-25% B over 20 min; flow 1.0 ml/minute; retention time 14.5 minutes, detected at 214 and 254 nm). Further characterisation was carried out using mass spectrometry, giving m/z value 1340.6 [M-3H+].

What is claimed is:

1. A compound of formula I having affinity for proteoglycans, and pharmaceutically acceptable salts thereof

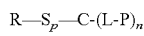

(I)

wherein

C represents a core unit linked to the L units and to the S unit when S is present or to the R moiety when S is not present, and which comprises amino acid residues selected from the group consisting of lysine, ornithine, and diaminopropionic acid, and optionally an amine;

L is the same or different and represents a bifunctional linker unit comprising a PEG linker, wherein said PEG linker is of formula (II)

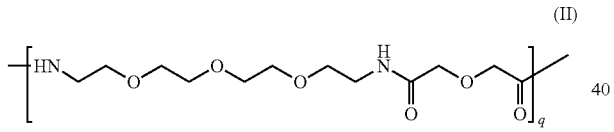

(II)

wherein q equals an integer from 1 to 10 and which binds to the carboxy and the amino entities of amino acids; or said PEG linker is of formula:

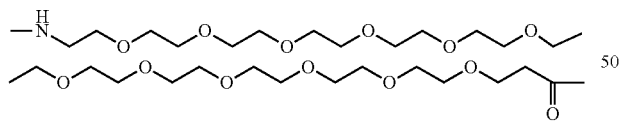

P is the same or different and represents a positively charged peptide unit comprising 2 to 8 positive charges and 2 to 20 amino acids, wherein at least one amino acid contains a guanidine group;

S represents a spacer unit;

R represents an imaging moiety comprising an imaging entity selected from the group consisting of:
(i) a radioactive metal ion;
(ii) a paramagnetic metal ion;
(iii) a gamma-emitting radioactive halogen;
(iv) a positron-emitting radioactive non-metal;
(v) a hyperpolarised NMR-active nucleus;
(vi) a reporter suitable for in vivo optical imaging; and
(vii) a β-emitter suitable for intravascular detection;

p represents an integer of 0 or 1; and
n represents an integer from 1 to 16.

2. The compound according to claim 1 wherein
S is present or absent and when present comprises an alkyl chain or a PEG unit;
n represents an integer of from 1 to 4.

3. The compound according to claim 1 wherein C comprises 2 to 16 amino acid residues.

4. The compound according to claim 1 wherein C comprises 2 to 4 lysine residues where the free terminal carboxyl residue is functionalised by the formation of an amide residue.

5. The compound according to claim 1 wherein P contains 2 to 16 amino acids where at least 2 amino acids have a positive charge at physiological pH.

6. The compound according to claim 1 wherein R is chosen from (i) a radioactive metal ion; (ii) a paramagnetic metal ion and (iii) a gamma-emitting radioactive halogen; and where the metal ion are bound by a chelating entity.

7. The compound according to claim 6 wherein R is a radioactive metal ion chelated by a chelator of formula (III)

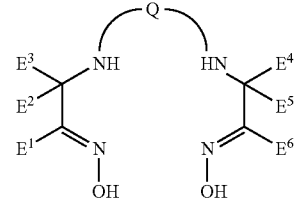

Formula (III)

where $E^1$-$E^6$ are each independently an R' group; each R' is H or $C_{1-10}$ alkyl, $C_{3-10}$ alkylaryl, $C_{2-10}$ alkoxyalkyl, $C_{1-10}$ hydroxyalkyl, $C_{1-10}$ fluoroalkyl, $C_{2-10}$ carboxyalkyl or $C_{1-10}$ aminoalkyl, or two or more R' groups that together with the atoms to which they are attached form a carbocyclic, heterocyclic, saturated or unsaturated ring, and wherein one or more of the R' groups is conjugated to the branching unit, and Q is a bridging group of formula -(J)$_f$; where f is 3, 4 or 5 and each J is independently —O—, —NR'— or —C(R')$_2$— provided that -(J)$_f$-contains a maximum of one J group which is —O— or —NR'—.

8. The compound according to claim 2 wherein
p represents an integer of 0;
and
n represents an integer of 2 or 4.

9. A compound of formula (I) selected from the group consisting of:

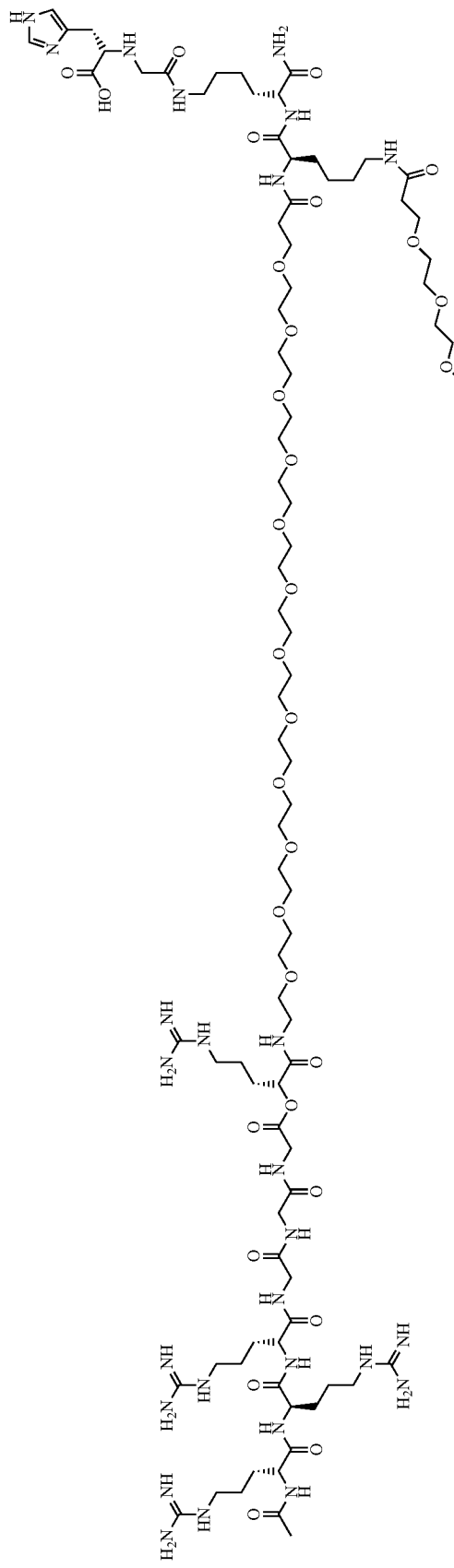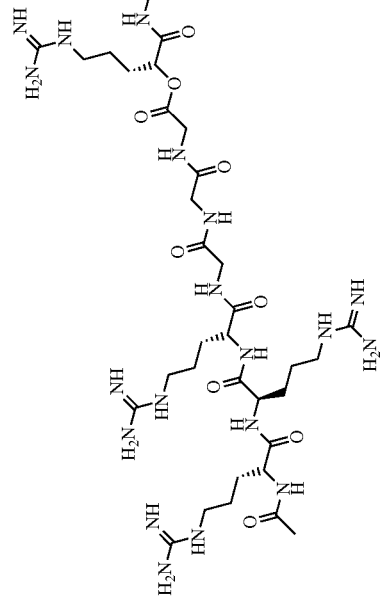

chelated with a radioactive metal entity; and

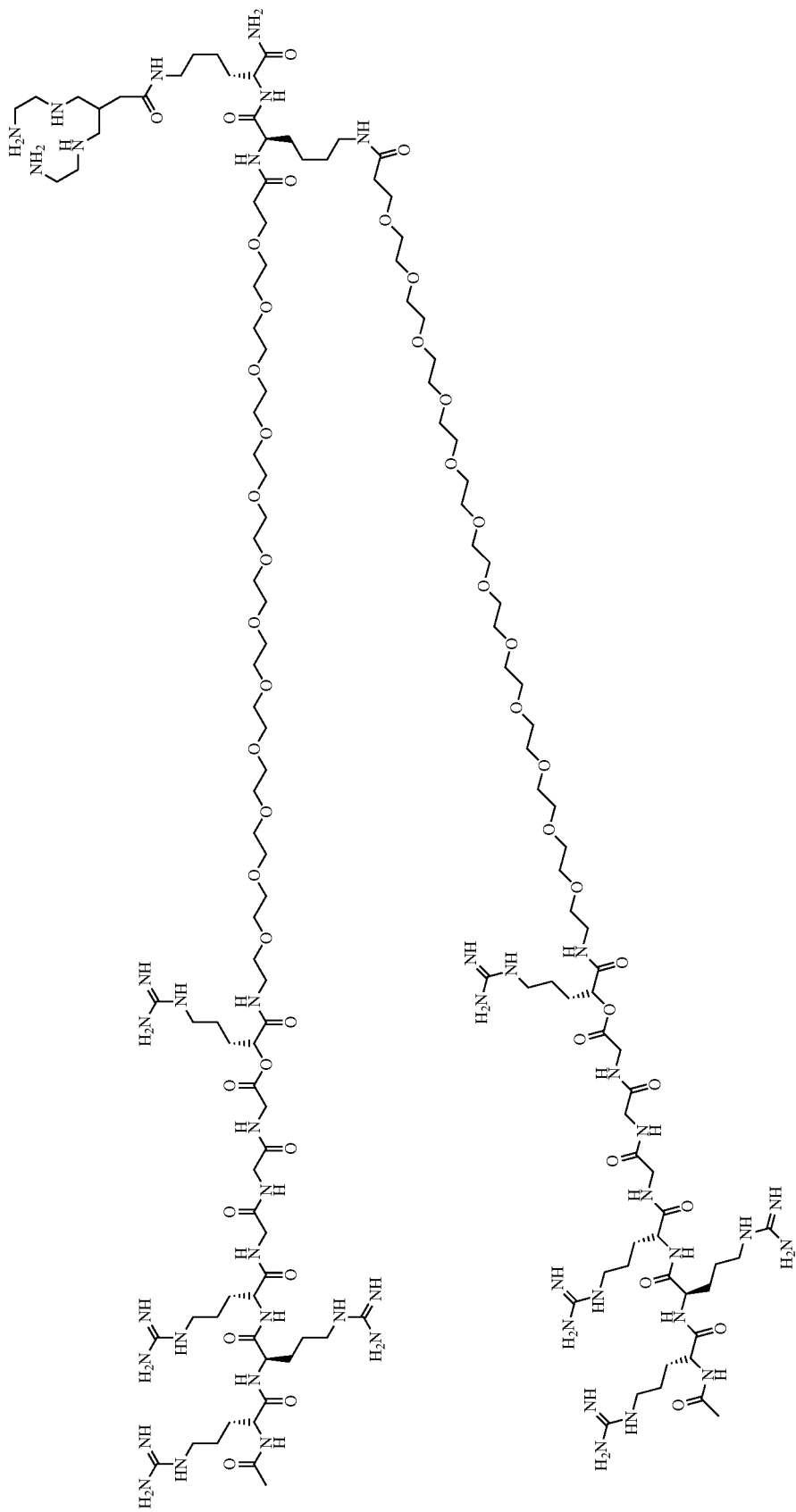

chelated with a radioactive metal entity.
10. A compound of formula (I) suitable for optical imaging selected from the group consisting of:
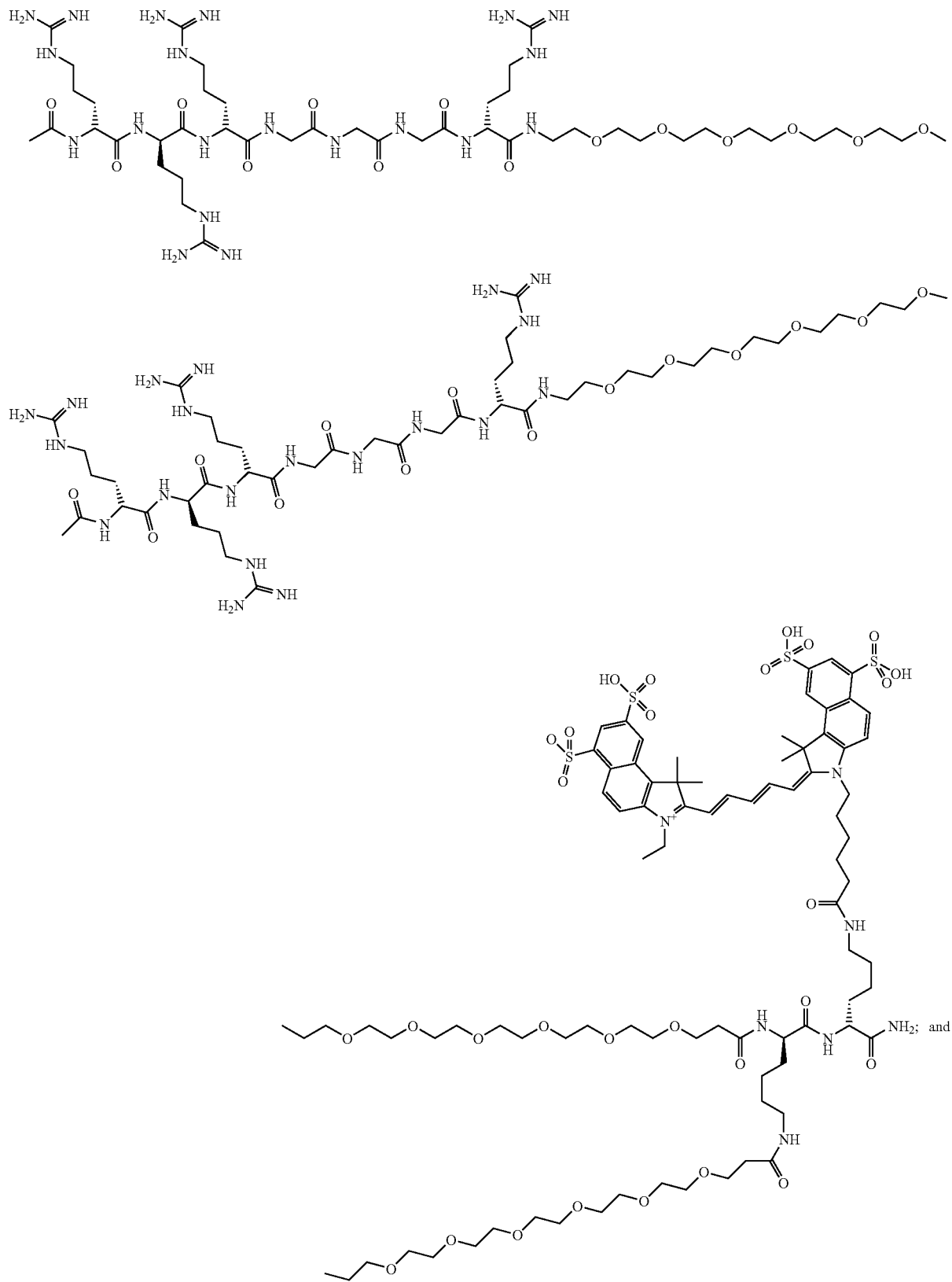

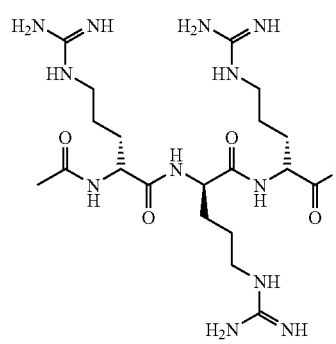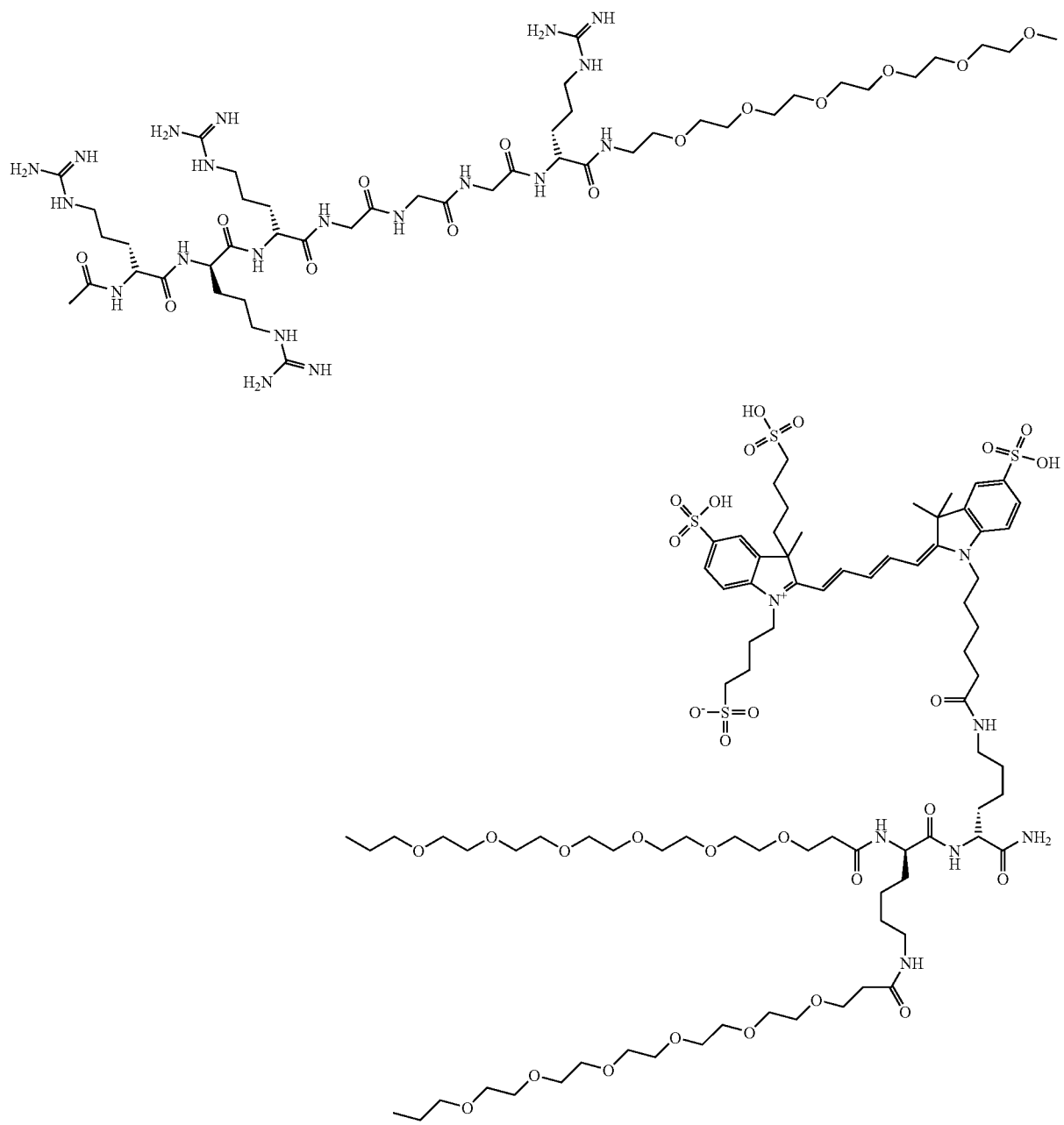

11. The compound according to claim 1 having affinity for heparan sulphate proteoglycans.

12. A pharmaceutical composition comprising a compound according to claim 1 and one or more pharmaceutically acceptable carriers or excipients.

13. A method of generating images of a human or animal body, wherein a compound as claimed in claim 1 is administered to a human or non-human body, and wherein an image of at least a part of said body is generated to which said compound has been distributed.

14. A method of generating images of a human or animal body previously administered with a pharmaceutical composition comprising a compound as claimed in claim 1 comprising generating an image of at least a part of said body to which said contrast agent composition has been distributed.

* * * * *